(12) United States Patent
Palti

(10) Patent No.: US 7,146,210 B2
(45) Date of Patent: Dec. 5, 2006

(54) APPARATUS AND METHOD FOR OPTIMIZING TUMOR TREATMENT EFFICIENCY BY ELECTRIC FIELDS

(75) Inventor: Yoram Palti, Haifa (IL)

(73) Assignee: Standen Ltd., Jersey (GB)

( * ) Notice: Subject to any disclaimer, the term of this patent is extended or adjusted under 35 U.S.C. 154(b) by 523 days.

(21) Appl. No.: 10/402,327

(22) Filed: Mar. 28, 2003

(65) Prior Publication Data

US 2004/0176804 A1 Sep. 9, 2004

Related U.S. Application Data

(63) Continuation-in-part of application No. 10/204,334, filed on Oct. 16, 2002.

(60) Provisional application No. 60/183,295, filed on Feb. 17, 2000.

(51) Int. Cl.
*A61N 1/18* (2006.01)
(52) U.S. Cl. .............................. 607/2; 607/154; 606/7; 606/32; 606/33
(58) Field of Classification Search ................. 607/33, 607/115, 154, 2; 606/7, 32–33, 41
See application file for complete search history.

(56) References Cited

U.S. PATENT DOCUMENTS

| | | | |
|---|---|---|---|
| 2,220,269 A | 11/1940 | Patzold et al. | |
| 4,016,886 A | 4/1977 | Doss et al. | |
| 4,121,592 A | 10/1978 | Whalley | |
| 4,263,920 A | 4/1981 | Tasto et al. | |
| 4,467,809 A | 8/1984 | Brighton | |
| 4,472,506 A | 9/1984 | Liburdy | |
| 4,622,952 A | 11/1986 | Gordon | |
| 4,626,506 A | 12/1986 | Zimmermann et al. | |
| 4,676,258 A | 6/1987 | Inokuchi et al. | |
| 4,822,470 A | 4/1989 | Chang | |
| 4,846,196 A | 7/1989 | Wiksell et al. | |
| 4,923,814 A | 5/1990 | Marshall | |
| 4,936,303 A | 6/1990 | Derwiler et al. | |
| 4,971,991 A | 11/1990 | Umemura et al. | |
| 5,099,756 A | 3/1992 | Franconi et al. | |
| 5,158,071 A | 10/1992 | Umemura et al. | |
| 5,236,410 A | 8/1993 | Granov et al. | |
| 5,312,813 A | 5/1994 | Costerton et al. | |
| 5,386,837 A | 2/1995 | Sterzer | |
| 5,389,069 A | 2/1995 | Weaver | |

(Continued)

FOREIGN PATENT DOCUMENTS

EP 0 330 797 A2 9/1989

(Continued)

OTHER PUBLICATIONS

Hofmann et al., "Electronic Genetic-Physical and Biological Aspects of Cellular Electomanipulation",IEEE Eng. in Med. and Biology Mag., Dec. 1986,p. 6-23,New York.

(Continued)

*Primary Examiner*—Jeffrey R. Jastrzab
*Assistant Examiner*—Bryan M. Jackson
(74) *Attorney, Agent, or Firm*—Proskauer Rose LLP

(57) ABSTRACT

The apparatus and method are designed to compute the optimal spatial and temporal characteristics for combating tumor growth within a body on the basis of cytological (as provided by biopsies, etc.) and anatomical data (as provided by CT, MRI, PET, etc.), as well as the electric properties of the different elements. On the basis of this computation, the apparatus applies the fields that have maximal effect on the tumor and minimal effect on all other tissues by adjusting both the field generator output characteristics and by optimal positioning of the insulated electrodes or isolects on the patient's body.

19 Claims, 29 Drawing Sheets

U.S. PATENT DOCUMENTS

| | | |
|---|---|---|
| 5,441,532 A | 8/1995 | Fenn |
| 5,441,746 A | 8/1995 | Chagnon |
| 5,468,223 A | 11/1995 | Mir |
| 5,606,971 A | 3/1997 | Sarvazyn |
| 5,674,267 A | 10/1997 | Mir et al. |
| 5,718,246 A | 2/1998 | Vona |
| 5,807,257 A | 9/1998 | Bridges |
| 5,976,092 A | 11/1999 | Chinn |
| 5,984,882 A | 11/1999 | Rosenschein et al. |
| 6,027,488 A | 2/2000 | Hofmann et al. |
| 6,043,066 A | 3/2000 | Mangano et al. |
| 6,055,453 A | 4/2000 | Hofmann et al. |
| 6,068,650 A | 5/2000 | Hofmann et al. |
| 6,096,020 A | 8/2000 | Hofmann et al. |
| 6,319,901 B1 | 11/2001 | Bernard et al. |
| 6,366,808 B1 | 4/2002 | Schroeppel et al. |
| 6,413,255 B1 | 7/2002 | Stern |
| 6,447,499 B1 | 9/2002 | Gray |
| 6,856,839 B1 * | 2/2005 | Litovitz ................. 607/100 |
| 2002/0193832 A1 | 12/2002 | Gray |
| 2003/0060866 A1 | 3/2003 | Chornenky et al. |
| 2003/0097152 A1 | 5/2003 | Palti |
| 2004/0068295 A1 | 4/2004 | Palti |
| 2004/0068296 A1 | 4/2004 | Palti |

FOREIGN PATENT DOCUMENTS

| | | |
|---|---|---|
| GB | 1 419 660 A1 | 12/1975 |
| GB | 2 026 322 A1 | 2/1980 |
| GB | 2 043 453 A1 | 10/1980 |
| WO | WO 01/60994 | 8/2001 |

OTHER PUBLICATIONS

Berg et al., "Electronic Field Effects on Biological Membranes:Electoincorporation and Electofusion",Ettore Maj. Inter. Science, 1987,p. 135-166,vol. 32, Phys. Science,New York.

Asbury et al., "Trapping of DNA in Nonuniform Oscillating Electic Fields", Biophysical Journal, Feb. 1998, p. 1024-1030,vol. 74, Seattle,WA.

* cited by examiner

FIG. 8
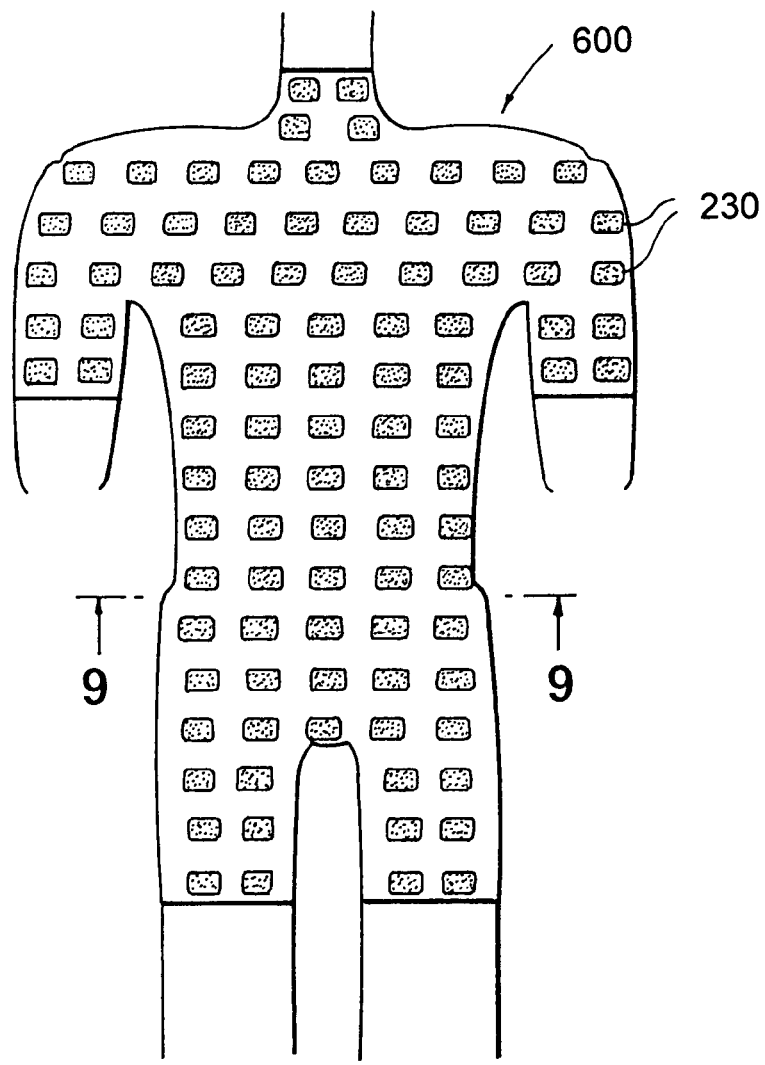
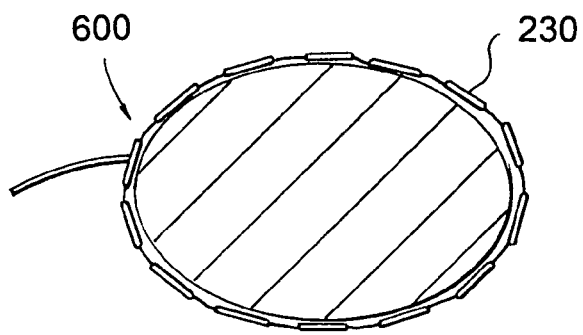
FIG. 9

Cross Section of Isolect With and Without a Protecting Net

APPARATUS AND METHOD FOR OPTIMIZING TUMOR TREATMENT EFFICIENCY BY ELECTRIC FIELDS

CROSS-REFERENCE TO RELATED APPLICATIONS

This application is a continuation-in-part of U.S. patent application Ser. No. 10/204,334, filed Oct. 16, 2002, which claims the benefit of U.S. patent application Ser. No. 60/183,295, filed Feb. 17, 2000, both of which are hereby incorporated by reference in their entirety.

FIELD OF THE INVENTION

The present invention relates to the selective destruction of rapidly dividing cells in a localized area, and more particularly, to an apparatus and method for optimizing the selective destruction of dividing cells by calculating the spatial and temporal distribution of electric fields for optimal treatment of a specific patient with a specific tumor taking into account its location and characteristics.

BACKGROUND OF THE INVENTION

All living organisms proliferate by cell division, including cell cultures, microorganisms (such as bacteria, mycoplasma, yeast, protozoa, and other single-celled organisms), fungi, algae, plant cells, etc. Dividing cells of organisms can be destroyed, or their proliferation controlled, by methods that are based on the sensitivity of the dividing cells of these organisms to certain agents. For example, certain antibiotics stop the multiplication process of bacteria.

The process of eukaryotic cell division is called "mitosis", which involves a number of distinct phases. During interphase, the cell replicates chromosomal DNA, which begins condensing in early prophase. At this point, centrioles (each cell contains 2) being moving towards opposite poles of the cell. In middle prophase, each chromosome is composed of duplicate chromatids. Microtubular spindles radiate from regions adjacent to the centrioles, which are closer to their poles. By late prophase, the centrioles have reached the poles, and some spindle fibers extend to the center of the cell, while others extend from the poles to the chromatids. The cells then move into metaphase, when the chromosomes move toward the equator of the cell and align in the equatorial plane. Next is early anaphase, during which time daughter chromatids separate from each other at the equator by moving along the spindle fibers toward a centromere at opposite poles. The cell begins to elongate along the axis of the pole; the pole-to-pole spindles elongate. Late anaphase occurs when the daughter chromosomes (as they are now called) each reach their respective opposite poles. At this point, cytokinesis begins as the cleavage furrow begins to form at the equator of the cell. In other words, late anaphase is the point at which pinching the cell membrane begins. During telophase, cytokinesis is nearly complete and spindles disappear. Only a relatively narrow membrane connection joins the two cytoplasms. Finally, the membranes separate fully, cytokinesis is complete and the cell returns to interphase.

In meiosis, the cell undergoes a second division, involving separation of sister chromosomes to opposite poles of the cell along spindle fibers, followed by formation of a cleavage furrow and cell division. However, this division is not preceded by chromosome replication, yielding a haploid germ cell.

It is known in the art that tumors, particularly malignant or cancerous tumors, grow very uncontrollably compared to normal tissue. Such expedited growth enables tumors to occupy an ever-increasing space and to damage or destroy tissue adjacent thereto. Furthermore, certain cancers are characterized by an ability to transmit cancerous "seeds", including single cells or small cell clusters (metastasises), to new locations where the metastatic cancer cells grow into additional tumors.

The rapid growth of tumors in general, and malignant tumors in particular, as described above, is the result of relatively frequent cell division or multiplication of these cells compared to normal tissue cells. The distinguishably frequent cell division of cancer cells is the basis for the effectiveness of existing cancer treatments, e.g., irradiation therapy and the use of various chemotherapeutic agents. Such treatments are based on the fact that cells undergoing division are more sensitive to radiation and chemo-therapeutic agents than non-dividing dells. Because tumor cells divide much more frequently than normal cells, it is possible, to a certain extent, to selectively damage or destroy tumor cells by radiation therapy and/or by chemotherapy. The actual sensitivity of cells to radiation, therapeutic agents, etc., is also dependent on specific characteristics of different types of normal or malignant cell type. Thus, unfortunately, the sensitivity of tumor cells is not sufficiently higher than that of many types of normal tissues. This diminishes the ability to distinguish between tumor cells and normal cells and, therefore, existing cancer treatments typically cause significant damage to normal tissues, thus limiting the therapeutic effectiveness of such treatments. Furthermore, the inevitable damage to other tissue renders treatments very traumatic to the patients and, often, patients are unable to recover from a seemingly successful treatment. Also, certain types of tumors are not sensitive at all to existing methods of treatment.

There are also other methods for destroying cells that do not rely on radiation therapy or chemotherapy alone. For example, ultrasonic and electrical methods for destroying tumor cells can be used in addition to or instead of conventional treatments. Electric fields and currents have been used for medical purposes for many years. The most common is the generation of electric currents in a human or animal body by application of an electric field by means of a pair of conductive electrodes between which a potential difference is maintained. These electric currents are used either to exert their specific effects, i.e., to stimulate excitable tissue, or to generate heat by flowing in the body since it acts as a resistor. Examples of the first type of application include the following: cardiac defibrillators, peripheral nerve and muscle stimulators, brain stimulators, etc. Currents are used for heating, for example, in devices for tumor ablation, ablation of malfunctioning cardiac or brain tissue, cauterization, relaxation of muscle rheumatic pain and other pain, etc.

Another use of electric fields for medical purposes involves the utilization of high frequency oscillating fields transmitted from a source that emits an electric wave, such as an RF wave or a microwave source that is directed at the part of the body that is of interest (i.e., target). In these instances, there is no electric energy conduction between the source and the body; but rather, the energy is transmitted to the body by radiation or induction. More specifically, the electric energy generated by the source reaches the vicinity of the body via a conductor and is transmitted from it through air or some other electric insulating material to the human body.

In a conventional electrical method, electrical current is delivered to a region of the target tissue using electrodes that are placed in contact with the body of the patient. The applied electrical current destroys substantially all cells in the vicinity of the target tissue. Thus, this type of electrical method does not discriminate between different types of cells within the target tissue and results in the destruction of both tumor cells and normal cells.

Electric fields that can be used in medical applications can thus be separated generally into two different modes. In the first mode, the electric fields are applied to the body or tissues by means of conducting electrodes. These electric fields can be separated into two types, namely (1) steady fields or fields that change at relatively slow rates, and alternating fields of low frequencies that induce corresponding electric currents in the body or tissues, and (2) high frequency alternating fields (above 1 MHz) applied to the body by means of the conducting electrodes. In the second mode, the electric fields are high frequency alternating fields applied to the body by means of insulated electrodes.

The first type of electric field is used, for example, to stimulate nerves and muscles, pace the heart, etc. In fact, such fields are used in nature to propagate signals in nerve and muscle fibers, central nervous system (CNS), heart, etc. The recording of such natural fields is the basis for the ECG, EEG, EMG, ERG, etc. The field strength in these applications, assuming a medium of homogenous electric properties, is simply the voltage applied to the stimulating/recording electrodes divided by the distance between them. These currents can be calculated by Ohm's law and can have dangerous stimulatory effects on the heart and CNS and can result in potentially harmful ion concentration changes. Also, if the currents are strong enough, they can cause excessive heating in the tissues. This heating can be calculated by the power dissipated in the tissue (the product of the voltage and the current).

When such electric fields and currents are alternating, their stimulatory power, on nerve, muscle, etc., is an inverse function of the frequency. At frequencies above 1–10 KHz, the stimulation power of the fields approaches zero. This limitation is due to the fact that excitation induced by electric stimulation is normally mediated by membrane potential changes, the rate of which is limited by the RC properties (time constants on the order of 1 ms) of the membrane.

Regardless of the frequency, when such current inducing fields are applied, they are associated with harmful side effects caused by currents. For example, one negative effect is the changes in ionic concentration in the various "compartments" within the system, and the harmful products of the electrolysis taking place at the electrodes, or the medium in which the tissues are imbedded. The changes in ion concentrations occur whenever the system includes two or more compartments between which the organism maintains ion concentration differences. For example, for most tissues, $[Ca^{++}]$ in the extracellular fluid is about $2 \times 10^{-3}$ M, while in the cytoplasm of typical cells its concentration can be as low as $10^{-7}$ M. A current induced in such a system by a pair of electrodes, flows in part from the extracellular fluid into the cells and out again into the extracellular medium. About 2% of the current flowing into the cells is carried by the $Ca^{++}$ ions. In contrast, because the concentration of intracellular $Ca^{++}$ is much smaller, only a negligible fraction of the currents that exits the cells is carried by these ions. Thus, $Ca^{++}$ ions accumulate in the cells such that their concentrations in the cells increases, while the concentration in the extracellular compartment may decrease. These effects are observed for both DC and alternating currents (AC). The rate of accumulation of the ions depends on the current intensity ion mobilities, membrane ion conductance, etc. An increase in $[Ca^{++}]$ is harmful to most cells and if sufficiently high will lead to the destruction of the cells. Similar considerations apply to other ions. In view of the above observations, long term current application to living organisms or tissues can result in significant damage. Another major problem that is associated with such electric fields, is due to the electrolysis process that takes place at the electrode surfaces. Here charges are transferred between the metal (electrons) and the electrolytic solution (ions) such that charged active radicals are formed. These can cause significant damage to organic molecules, especially macromolecules and thus damage the living cells and tissues.

In contrast, when high frequency electric fields, above 1 MHz and usually in practice in the range of GHz, are induced in tissues by means of insulated electrodes, the situation is quite different. These type of fields generate only capacitive or displacement currents, rather than the conventional charge conducting currents. Under the effect of this type of field, living tissues behave mostly according to their dielectric properties rather than their electric conductive properties. Therefore, the dominant field effect is that due to dielectric losses and heating. Thus, it is widely accepted that in practice, the meaningful effects of such fields on living organisms, are only those due to their heating effects, i.e., due to dielectric losses.

In U.S. Pat. No. 6,043,066 ('066) to Mangano, a method and device are presented which enable discrete objects having a conducting inner core, surrounded by a dielectric membrane to be selectively inactivated by electric fields via irreversible breakdown of their dielectric membrane. One potential application for this is in the selection and purging of certain biological cells in a suspension. According to this patent, an electric field is applied for targeting selected cells to cause breakdown of the dielectric membranes of these tumor cells, while purportedly not adversely affecting other desired subpopulations of cells. The cells are selected on the basis of intrinsic or induced differences in a characteristic electroporation threshold. The differences in this threshold can depend upon a number of parameters, including the difference in cell size.

The method of the '066 patent is therefore based on the assumption that the electroporation threshold of tumor cells is sufficiently distinguishable from that of normal cells because of differences in cell size and differences in the dielectric properties of the cell membranes. Based upon this assumption, the larger size of many types of tumor cells makes these cells more susceptible to electroporation and thus, it may be possible to selectively damage only the larger tumor cell membranes by applying an appropriate electric field. One disadvantage of this method is that the ability to discriminate is highly dependent upon on cell type, for example, the size difference between normal cells and tumor cells is significant only in certain types of cells. Another drawback of this method is that the voltages which are applied may damage some of the normal cells and may not damage all of the tumor cells because the differences in size and membrane dielectric properties are largely statistical and the actual cell geometries and dielectric properties may vary significantly.

What is needed in the art and has heretofore not been available is an apparatus for destroying dividing cells, wherein the apparatus better discriminates between dividing cells, including single-celled organisms, and non-dividing cells and is capable of selectively destroying the dividing cells or organisms with substantially no affect on the non-dividing cells or organisms and which can be configured to adopt its characteristics and spatial distribution within the patient's body so as to optimally destroy a specific tumor or tumors in a patient. The data regarding the specific tumor can be provided by conventional techniques, such as CT, MRI, etc., imaging of the tumor and its surroundings, as well as other means for characterization of the tumors.

SUMMARY OF THE INVENTION

An apparatus and related method for use in a number of different applications for optimization of the selective electric fields in destroying cells undergoing growth and division are provided. This includes cell (particularly tumor cells) in living tissues and organisms or other complex structures. The apparatus and method are designed to compute the optimal spatial and temporal characteristics for combating tumor growth within a body on the basis of cytological (as provided by biopsies, etc.) and anatomical data (as provided by CT, MRI, PET, etc.), as well as the electric properties of the different elements. On the basis of this computation, the apparatus applies the fields that have maximal effect on the tumor and minimal effect on all other tissues by adjusting both the field generator output characteristics and by optimal positioning of the insulated electrodes or isolects on the patient's body. For example and as will be described in greater detail hereinafter, the isolects are directly applied to the patient or by means of probes or pieces of clothing that are worn over the tumor area. In either case, the apparatus can activate the selected set of electrodes (isolects) to achieve optimal effect.

A major use of the method and apparatus of the present invention is in treatment of tumors by selective destruction of tumor cells with substantially no affect on normal tissue cells and, thus, the invention is described below in the context of selective destruction of tumor cells. It should be appreciated however that, for the purpose of the description that follows, the term "cell" may also refer to single-celled organisms (eubacteria, bacteria, yeast, protozoa), multi-celled organisms (fungi, algae, mold), and plants as or parts thereof that are not normally classified as "cells". The method of the present invention enables selective destruction of tumor cells, or other organisms, by selective destruction of cells undergoing division in a way that is more effective and more accurate (e.g., more adaptable to be aimed at specific targets) than existing methods. Further, the method of the present invention causes minimal damage, if any, to normal tissue and, thus, reduces or eliminates many side-effects associated with existing selective destruction methods, such as radiation therapy and chemotherapy. The selective destruction of dividing cells in accordance with the method of the present invention does not depend on the sensitivity of the cells to chemical agents or radiation. Instead, the selective destruction of dividing cells is based on distinguishable geometrical characteristics of cells undergoing division, in comparison to non-dividing cells, regardless of the cell geometry of the type of cells being treated. As well as the electric properties of the special apparatus associated with cell division (microtubules, tubulin filaments, etc.).

In an embodiment of the present invention, cell geometry-dependent selective destruction of living tissue is performed by inducing a non-homogenous electric field in the cells, as described below.

It has been observed by the present inventor that, while different cells in their non-dividing state may have different shapes, e.g., spherical, ellipsoidal, cylindrical, "pancake-like", etc., the division process of practically all cells is characterized by development of a "cleavage furrow" in late anaphase and telophase. This cleavage furrow is a slow constriction of the cell membrane (between the two sets of daughter chromosomes) which appears microscopically as a growing cleft (e.g., a groove or notch) that gradually separates the cell into two new cells. During the division process, there is a transient period (telophase) during which the cell structure is basically that of two sub-cells interconnected by a narrow "bridge" formed of the cell material. The division process is completed when the "bridge" between the two sub-cells is broken. The selective destruction of tumor cells using the present electronic apparatus utilizes this unique geometrical feature of dividing cells.

When a cell or a group of cells are under natural conditions or environment, i.e., part of a living tissue, they are disposed surrounded by a conductive environment consisting mostly of an electrolytic inter-cellular fluid and other cells that are composed mostly of an electrolytic intra-cellular liquid. When an electric field is induced in the living tissue, by applying an electric potential across the tissue, an electric field is formed in the tissue and the specific distribution and configuration of the electric field lines defines the direction of charge displacement, or paths of electric currents in the tissue, if currents are in fact induced in the tissue. The distribution and configuration of the electric field is dependent on various parameters of the tissue, including the geometry and the electric properties of the different tissue components, and the relative conductivities, capacities and dielectric constants (that may be frequency dependent) of the tissue components.

The electric current flow pattern for cells undergoing division is very different and unique as compared to non-dividing cells. Such cells including first and second sub-cells, namely an "original" cell and a newly formed cell, that are connected by a cytoplasm "bridge" or "neck". The currents penetrate the first sub-cell through part of the membrane ("the current source pole"); however, they do not exit the first sub-cell through a portion of its membrane closer to the opposite pole ("the current sink pole"). Instead, the lines of current flow converge at the neck or cytoplasm bridge, whereby the density of the current flow lines is greatly increased. A corresponding, "mirror image", process that takes place in the second sub-cell, whereby the current flow lines diverge to a lower density configuration as they depart from the bridge, and finally exit the second sub-cell from a part of its membrane closes to the current sink.

When a polarizable object is placed in a non-uniform converging or diverging field, electric forces act on it and pull it towards the higher density electric field lines. In the case of dividing cell, electric forces are exerted in the direction of the cytoplasm bridge between the two cells. Since all intercellular organelles and macromolecules are polarizable, they are all force towards the bridge between the two cells. The field polarity is irrelevant to the direction of the force and, therefore, an alternating electric having specific properties can be used to produce substantially the same effect. It will also be appreciated that the concentrated and inhomogeneous electric field present in or near the bridge or neck portion in itself exerts strong forces on charges and natural dipoles and can lead to the disruption of structures associated with these members.

The movement of the cellular organelles towards the bridge disrupts the cell structure and results in increased pressure in the vicinity of the connecting bridge membrane. This pressure of the organelles on the bridge membrane is expected to break the bridge membrane and, thus, it is expected that the dividing cell will "explode" in response to this pressure. The ability to break the membrane and disrupt other cell structures can be enhanced by applying a pulsating alternating electric field that has a frequency from about 50 KHz to about 500 KHz. When this type of electric field is applied to the tissue, the forces exerted on the intercellular organelles have a "hammering" effect, whereby force pulses (or beats) are applied to the organelles numerous times per second, enhancing the movement of organelles of different sizes and masses towards the bridge (or neck) portion from both of the sub-cells, thereby increasing the probability of breaking the cell membrane at the bridge portion. The forces exerted on the intracellular organelles also affect the organelles themselves and may collapse or break the organelles.

According to one exemplary embodiment, the apparatus for applying the electric field is an electronic apparatus that generates the desired electric signals in the shape of waveforms or trains of pulses. The electronic apparatus includes a generator that generates an alternating voltage waveform at frequencies in the range from about 50 KHz to about 500 KHz. The generator is operatively connected to conductive leads which are connected at their other ends to insulated conductors/electrodes (also referred to as isolects) that are activated by the generated waveforms. The generator may provide each electrode with a specific selected waveform that is calculated for field distribution that gives optimal results. This can be represented in the form of an Optimal Map. The insulated electrodes consist of a conductor in contact with a dielectric (insulating layer) that is in contact with the conductive tissue, thus forming a capacitor. The electric fields that are generated by the present apparatus can be applied in several different modes depending upon the precise treatment application and physiological and anatomical characteristics of the patient's parts of the body undergoing treatment.

BRIEF DESCRIPTION OF THE DRAWINGS

FIG. 8 is a front elevation view of an undershirt incorporating the present apparatus being worn over a human body;

FIG. 9 is a cross-sectional taken along the line 9—9;

FIG. 19 is a cross-sectional illustration of a skin patch incorporating the apparatus of FIG. 5 and for placement on a skin surface for treating a tumor or the like;

FIG. 20 is a cross-sectional illustration of the insulated electrodes implanted within the body for treating a tumor or the like;

FIG. 21 is a cross-sectional illustration of the insulated electrodes implanted within the body for treating a tumor or the like;

FIG. 26 is a cross-sectional view of insulated electrodes incorporated into a hat according to a first embodiment for placement on a head for treating an intra-cranial tumor or the like;

FIG. 29 is a cross-sectional top view of an article of clothing having the insulated electrodes incorporated therein for treating a tumor or the like;

FIG. 31 is a cross-sectional view of a probe according to one embodiment for being disposed internally within the body for treating a tumor or the like;

DETAILED DESCRIPTION OF PREFERRED EMBODIMENTS THE INVENTION

Figure 1A:
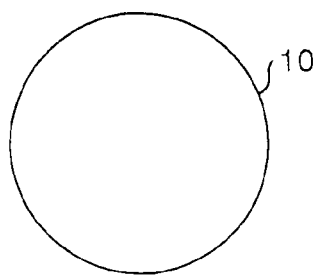
FIGS. 1A–1E are simplified, schematic, cross-sectional, illustrations of various stages of a cell division process.
Figure 1B:
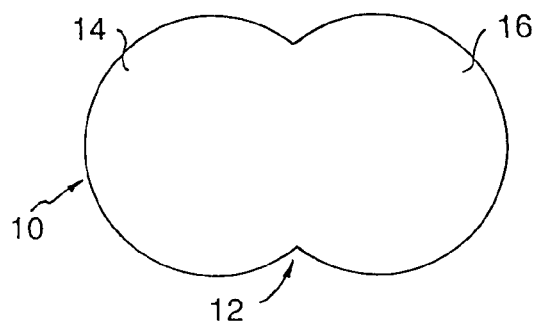
Figure 1C:
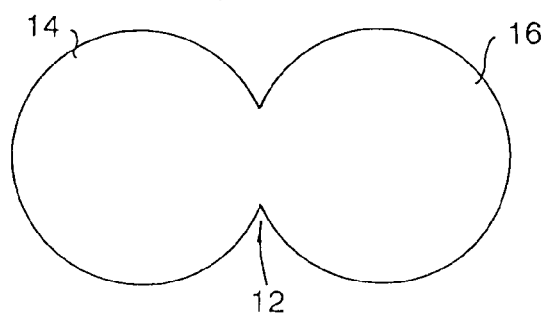
Figure 1D:
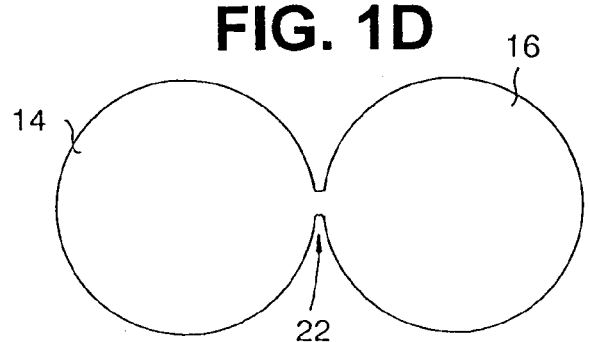

Reference is made to FIGS. 1A–1E which schematically illustrate various stages of a cell division process. FIG. 1A shows a cell 10 at its normal geometry, which may be generally spherical (as shown in the drawings), ellipsoidal, cylindrical, "pancake" like, or any other cell geometry, as is known in the art. FIGS. 1B–1D show cell 10 during different stages of its division process, which results in the formation of two new cells 18 and 20, shown in FIG. 1E.

Figure 1E:
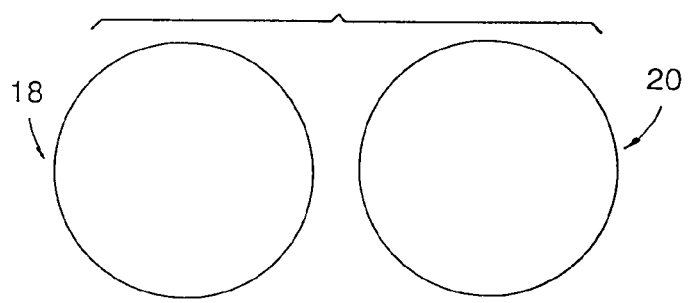

As shown in FIGS. 1B–1D, the division process of cell 10 is characterized by a slowly growing cleft 12 which gradually separates cell 10 into two units, namely, sub-cells 14 and 16, which eventually evolve into new cells 18 and 20 (FIG. 1E). As shown specifically in FIG. 1D, the division process is characterized by a transient period during which the structure of cell 10 is basically that of the two sub-cells 14 and 16 interconnected by a narrow "bridge" 22 containing cell material (cytoplasm surrounded by cell membrane).

Figure 2A:
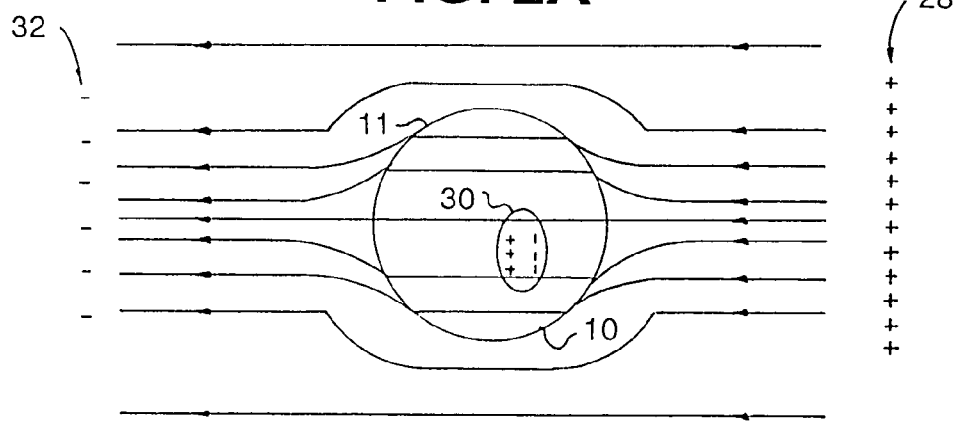
FIGS. 2A and 2B are schematic illustrations of a non-dividing cell being subjected to an electric field, in accordance with an embodiment of the present invention.
Figure 2B:
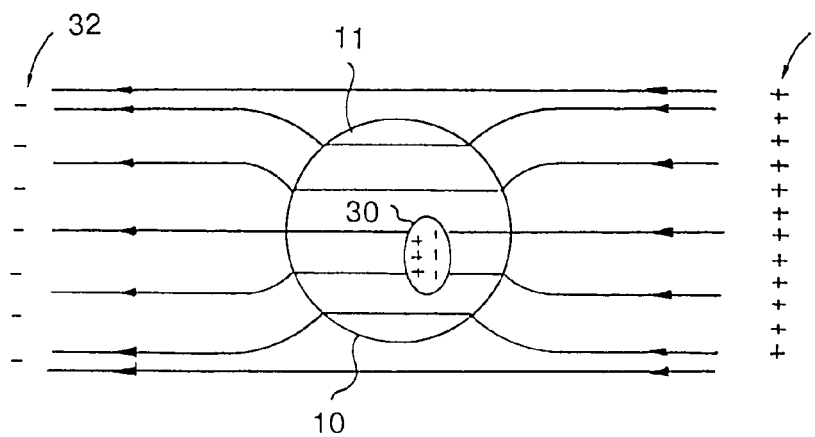

Reference is now made to FIGS. 2A and 2B, which schematically illustrate non-dividing cell 10 being subjected to an electric field produced by applying an alternating electric potential, at a relatively low frequency and at a relatively high frequency, respectively. Cell 10 includes intracellular organelles, e.g., a nucleus 30. Alternating electrical potential is applied across electrodes 28 and 32 that may be attached externally to a patient at a predetermined region, e.g., in the vicinity of a tumor being treated. When cell 10 is under natural conditions, i.e., part of a living tissue, it is disposed in a conductive environment (hereinafter referred to as a "volume conductor") consisting mostly of electrolytic inter-cellular liquid. When an electric potential is applied across electrode 28 and 32, some of the field lines of the resultant electric field (or the current induced in the tissue in response to the electric field) penetrate cell 10, while the rest of the field lines (or induced current) flow in the surrounding medium. The specific distribution of the electric field lines, which is substantially consistent with the direction of current flow in this case, depends on the geometry and the electric properties of the system components, e.g., the relative conductivities and dielectric constants of the system components, that may be frequency dependent. For low frequencies, e.g., frequencies considerably lower than 10 kHz, the conductance properties of the components dominate the current flow, and the field distribution is generally as depicted in FIG. 2A. At higher frequencies, e.g., at frequencies of between 10 kHz and 1 MHz, the dielectric properties of the components become more significant and eventually dominate the field distribution, resulting in field distribution lines as depicted generally in FIG. 2B.

For constant (i.e., DC) electric fields or relatively low frequency alternating electric fields, for example, frequencies under 10 kHz, the dielectric properties of the various components are not significant in determining and computing the field distribution. Therefore, as a first approximation, with regard to the electric field distribution, the system can be reasonably represented by the relative impedances of its various components. Under this approximation, the intercellular (i.e., extracellular) fluid and the intracellular fluid have a relatively low impedance, while the cell membrane 11 has a relatively high impedance. Thus, under low frequency conditions, only a fraction of the electric field lines (or currents induced by the electric field) penetrate membrane 11 of cell 10. At relatively high frequencies (e.g., 10 kHz–1 MHz), in contrast, the impedance of membrane 11 relative to the intercellular and intracellular fluids decreases and, thus, the fraction of currents penetrating the cells increases significantly. It should be noted that at very high frequencies, i.e., above 1 MHz, the membrane capacitance may short the membrane resistance and, therefore, the total membrane resistance may become negligible.

In any of the embodiments described above, the electric field lines (or induced currents) penetrate cell 10 from a portion of membrane 11 closest to one of the electrodes generating the current, e.g., closest to positive electrode 28 (also referred to herein as "source"). The current flow pattern across cell 10 is generally uniform because, under the above approximation, the field induced inside the cell is substantially homogenous. The currents exit cell 10 through a portion of membrane 11 closest to the opposite electrode, e.g., negative electrode 32 (also referred to herein as "sink").

The distinction between field lines and current flow may depend on a number of factors, for example, on the frequency of the applied electric potential and on whether electrodes 28 and 32 are electrically insulated. For insulated electrodes applying a DC or low frequency alternating voltage, there is practically no current flow along the lines of the electric field. At higher frequencies, displacement currents are induced in the tissue due to charging and discharging of the cell membranes (which act as capacitors to a certain extent), and such currents follow the lines of the electric field. Fields generated by non-insulated electrodes, in contrast, always generate some form of current flow, specifically, DC or low frequency alternating fields generate conductive current flow along the field lines, and high frequency alternating fields generate both conduction and displacement currents along the field lines. It should be appreciated, however, that movement of polarizable intracellular organelles according to the present invention (as described below) is not dependent on actual flow of current and, therefore, both insulated and non-insulated electrodes may be used efficiently in conjunction with the present invention. Nevertheless, insulated electrodes have the advantage of lower power consumption and causing less heating of the treated regions.

According to one exemplary embodiment, the electric fields that are used in the present apparatus are alternating fields having frequencies that in the range from about 50 KHz to about 500 KHz, and preferably from about 100 KHz to about 300 KHz. For ease of discussion, these type of electric fields are also referred to hereinafter as "TC fields", which is an abbreviation of "Tumor Curing electric fields", since these electric fields fall into an intermediate category (between high and low frequency ranges) that have bioeffective field properties, while having no meaningful stimulatory and thermal effects. These frequencies are sufficiently low so that the system behavior is determined by the system's "Ohmic" (conductive) properties but sufficiently high enough not to have any stimulation effect on excitable tissues. Such a system consists of two types of elements, namely, the intercellular, or extracellular fluid, or medium and the individual cells. The intercellular fluid is mostly an electrolyte with a specific resistance of about 40–100 ohm*cm. As mentioned above, the cells are characterized by three elements, namely (1) a thin, highly electric resistive membrane that coats the cell; (2) internal cytoplasm that is mostly an electrolyte that contains numerous macromolecules and micro-organelles, including the nucleus; and (3) membranes, similar in their electric properties to the cell membranes, cover the micro-organelles.

When this type of system is subjected to the present TC fields (e.g., alternating electric fields in the frequency range of 100 KHz–300 KHz), most of the lines of the electric field and currents tend away from the cells because of the high resistive cell membrane and therefore, the lines remain in the extracellular conductive medium. In the above recited frequency range, the actual fraction of electric field or currents that penetrate the cells is a strong function of the frequency.

FIG. 2 schematically depicts the resulting field distribution in the system. As illustrated, the lines of force, which also depict the lines of potential current flow across the cell volume mostly in parallel with the undistorted lines of force (the main direction of the electric field). In other words, the field inside the cells is mostly homogeneous. In practice, the fraction of the field or current that penetrates the cells is determined by the cell membrane impedance value relative to that of the extracellular fluid. Since the equivalent electric circuit of the cell membrane is that of a resistor and capacitor in parallel, the impedance is function of the frequency. The higher the frequency, the lower the impedance, the larger the fraction of penetrating current and the smaller the field distortion.

As previously mentioned, when cells are subjected to relatively weak electric fields and currents that alternate at high frequencies, such as the present TC fields having a frequency in the range of 50 KHz to 500 KHz, they have no effect on the non-dividing cells. While the present TC fields have no detectable effect on such systems, the situation becomes different in the presence of dividing cells.

Figure 3A:
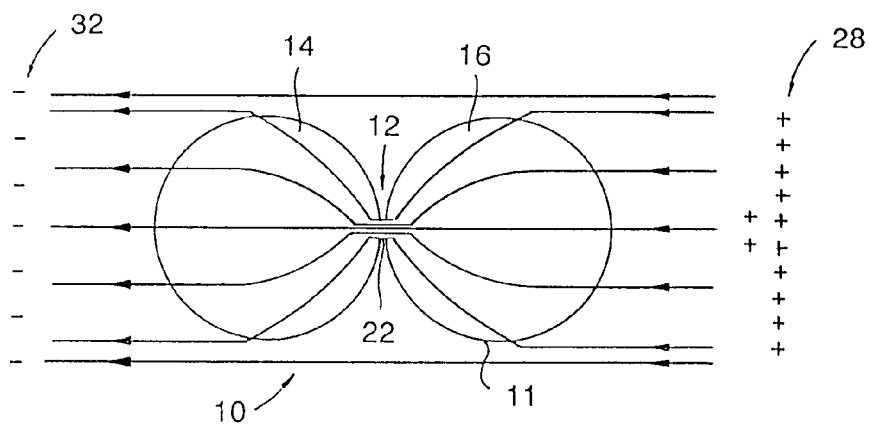
FIGS. 3A, 3B and 3C are schematic illustrations of a dividing cell being subjected to an electric field, resulting in destruction of the cell (FIG. 3C), in accordance with an embodiment of the present invention.
Figure 3B:
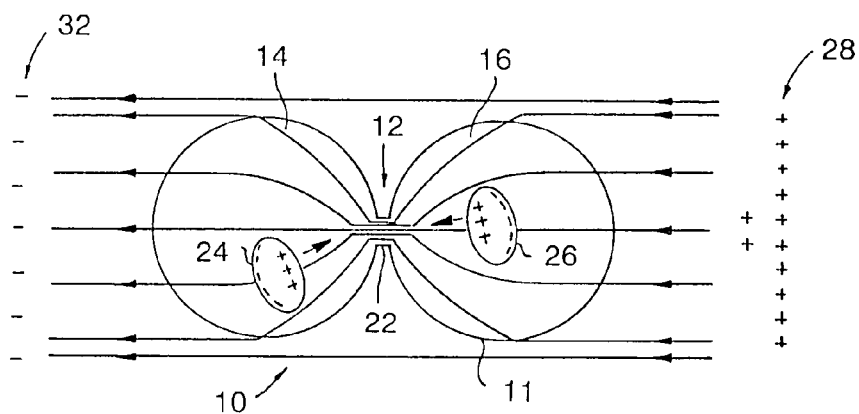
Figure 3C:
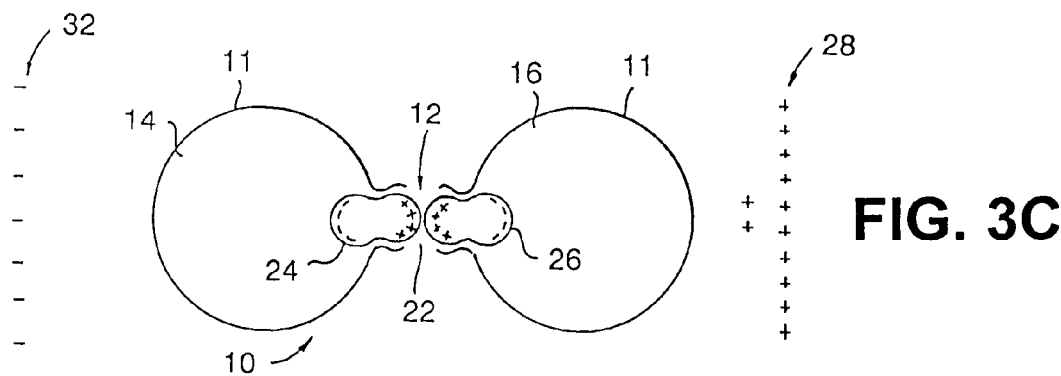

Reference is now made to FIGS. 3A–3C which schematically illustrate the electric current flow pattern in cell 10 during its division process, under the influence of high frequency alternating electric field in accordance with an embodiment of the invention. The field lines or induced currents penetrate cell 10 through a part of the membrane of sub-cell 16 closer to electrode 28. However, they do not exit through the cytoplasm bridge 22 that connects sub-cell 16 with the newly formed yet still attached sub-cell 14, or through a part of the membrane in the vicinity of bridge 22. Instead, the electric field or current flow lines—that are relatively widely separated in sub-cell 16—converge as they approach bridge 22 (also referred to as "neck" 22) and, thus, the current/field line density within neck 22 is increased dramatically. A "mirror image" process takes place in sub-cell 14, whereby the converging field lines in bridge 22 diverge as they approach the exit region of sub-cell 14.

It should be appreciated by persons skilled in the art that homogenous electric fields do not exert a force on electrically neutral objects, i.e., objects having substantially zero net charge, although such objects may become polarized. However, under a non-uniform, converging electric field, as shown in FIGS. 3A–3C, electric forces are exerted on polarized objects, moving them in the direction of the higher density electric field lines. It will be appreciated that the concentrated electric field that is present in the neck or bridge area in itself exerts strong forces on charges and natural dipoles and can disrupt structures that are associated therewith. One will understand that similar net forces act on charges in an alternating field, again in the direction of the field of higher intensity.

In the configuration of FIGS. 3A and 3B, the direction of movement of polarized objects is towards the higher density electric filed lines, i.e., towards the cytoplasm bridge 22 between sub-cells 14 and 16. It is known in the art that all intracellular organelles, for example, nuclei 24 and 26 of sub-cells 14 and 16, respectively, are polarizable and, thus, such intracellular organelles will be electrically forced in the direction of bridge 22. Since the movement is always from the lower density currents to the higher density currents, regardless of the field polarity, the forces applied by the alternating electric field to organelles such as nuclei 24 and 26 are always in the direction of bridge 22. A comprehensive description of such forces and the resulting movement of macromolecules or intracellular organelles, a phenomenon referred to as dielectrophoresis, is described extensively in the literature, for example, in C. L. Asbury & G. van den Engh, Biophys. J. 74, 1024–1030, 1998, the disclosure of which is incorporated herein by reference.

The movement of organelles 24 and 26 towards bridge 22 disrupts the structure of the dividing cell and, eventually, the pressure of the converging organelles on bridge membrane 22 results in breakage of cell membrane 11 at the vicinity of bridge 22, as shown schematically in FIG. 3C. The ability to break membrane 11 at bridge 22 and to otherwise disrupt the cell structure and organization may be enhanced by applying a pulsating AC electric field, rather than a steady AC field. When a pulsating field is applied, the forces acting on organelles 24 and 26 may have a "hammering" effect, whereby pulsed forces beat on the intracellular organelles at a desired rhythm, e.g., a pre-selected number of times per second. Such "hammering" is expected to enhance the movement of intracellular organelles towards neck 22 from both sub cells 14 and 16), thereby increasing the probability of breaking cell membrane 11 in the vicinity of neck 22.

Figure 4:
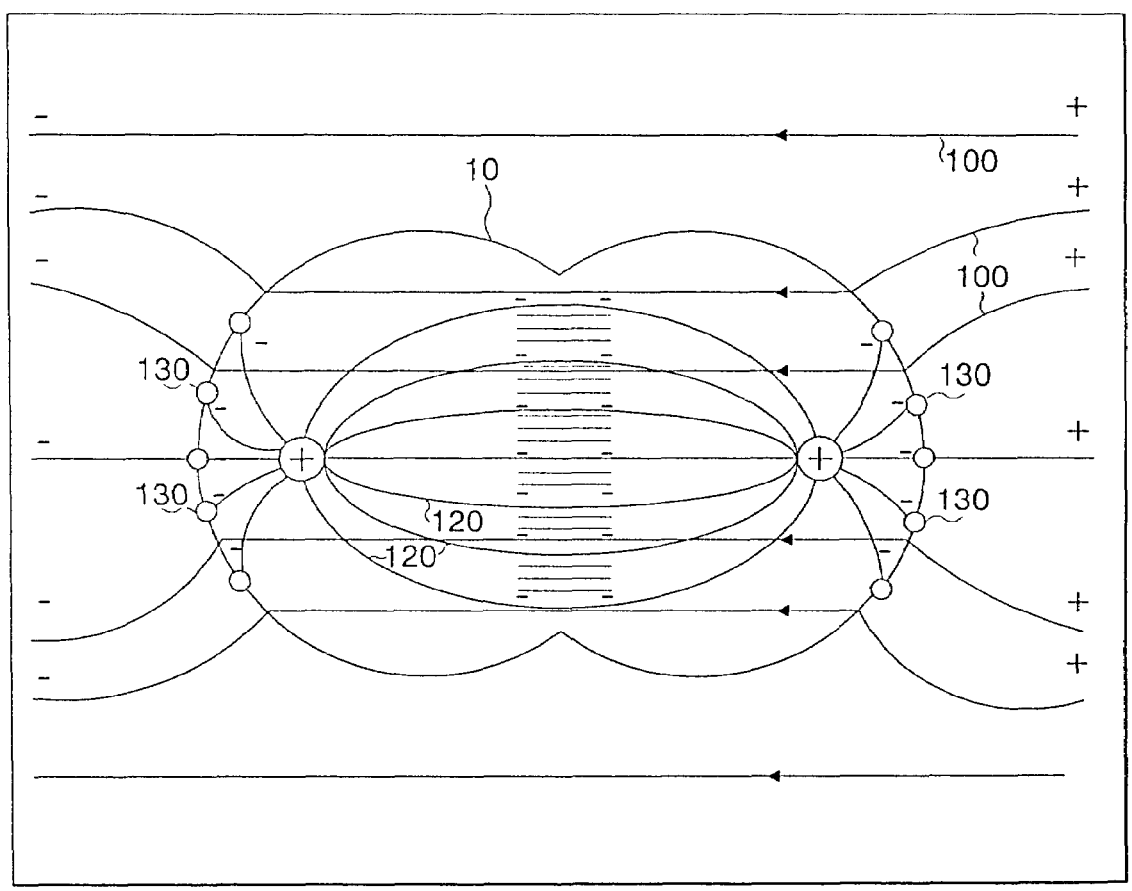
FIG. 4 is a schematic illustration of a dividing cell at one stage being subjected to an electric field.

A very important element, which is very susceptible to the special fields that develop within the dividing cells is the microtubule spindle that plays a major role in the division process. In FIG. 4, a dividing cell 10 is illustrated, at an earlier stage as compared to FIGS. 3A and 3B, under the influence of external TC fields (e.g., alternating fields in the frequency range of about 100 KHz to about 300 KHz), generally indicated as lines 100, with a corresponding spindle mechanism generally indicated at 120. The lines 120 are microtubules that are known to have a very strong dipole moment. This strong polarization makes the tubules susceptible to electric fields. Their positive charges are located at two centrioles while two sets of negative poles are at the center of the dividing cells and the other pair is at the points of attachment of the microtubules to the cell membrane, generally indicated at 130. This structure forms sets of double dipoles and therefore, they are susceptible to fields of different directions. It will be understood that the effects of the TC fields on the dipoles does not depend on the formation of the bridge (neck) and thus, the dipoles are influenced by the TC fields prior to the formation of the bridge (neck).

Since the present apparatus, as described in greater detail hereinafter, utilizes insulated electrodes, the above-mentioned negative effects obtained when conductive electrodes are used, i.e., ion concentration changes in the cells and the formation of harmful agents by electrolysis, do not occur when the present apparatus is used. This is because, in general, no actual transfer of charges takes place between the electrodes and the medium and there is no charge flow in the medium where the currents are capacitive, i.e., are expressed only as rotation of charges, etc.

Figure 5:
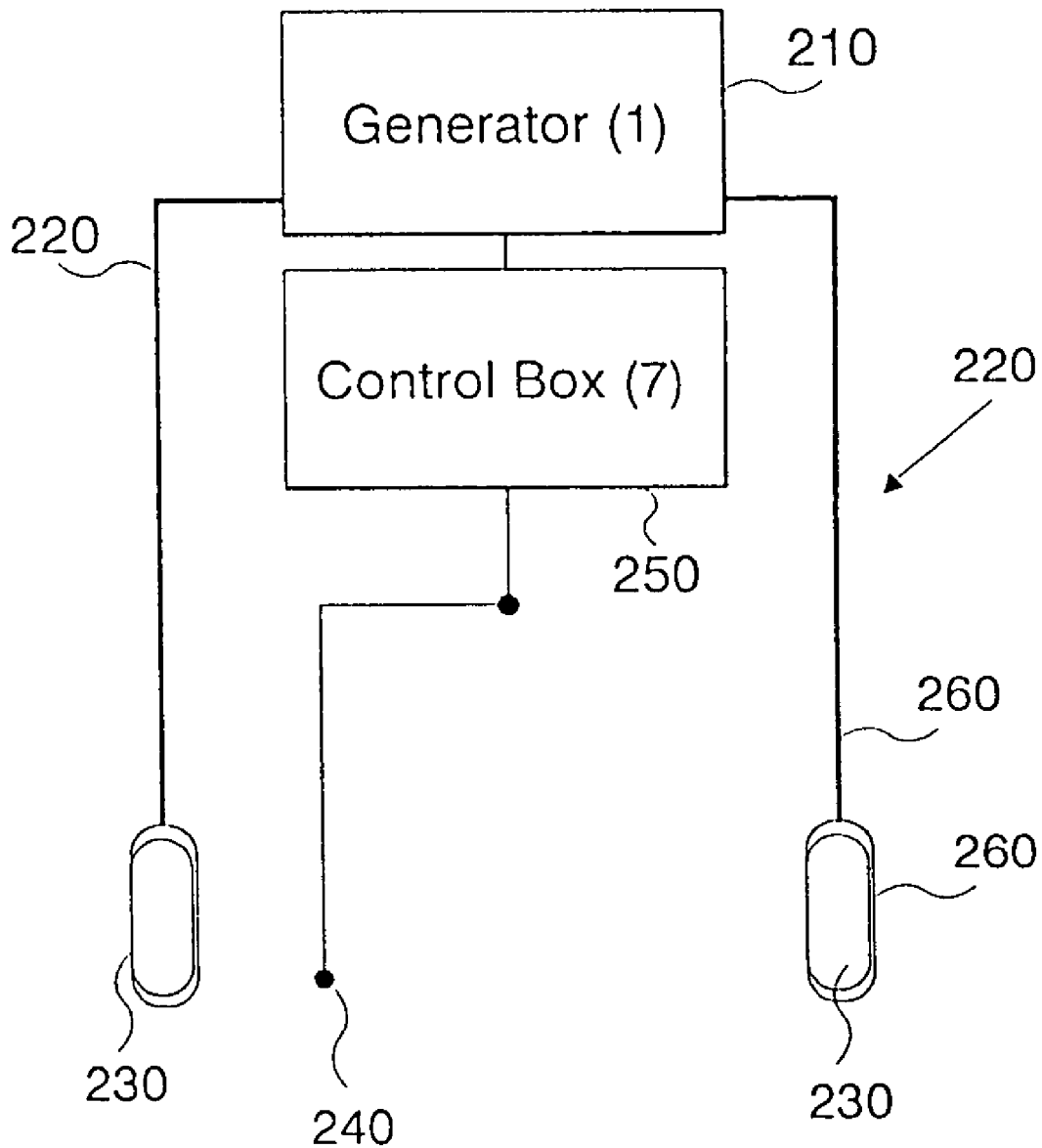
FIG. 5 is a schematic block diagram of an apparatus for applying an electric field according to one exemplary embodiment for selectively destroying cells.

Turning now to FIG. 5, the TC fields described above that have been found to advantageously destroy tumor cells are generated by an electronic apparatus 200. FIG. 5 is a simple schematic diagram of the electronic apparatus 200 illustrating the major components thereof. The electronic apparatus 200 generates the desired electric field signals (TC signals) in the shape of waveforms or trains of pulses. The apparatus 200 includes a generator 210 and a set of pairs of conductive leads 220 that are attached at one end thereof to the generator 210. The opposite ends of the leads 220 are connected to the insulated conductors 230 that are activated by the electric signals (e.g., waveforms). The insulated conductors 230 are also referred to hereinafter as "isolects" 230. Optionally and according to one exemplary embodiment, the apparatus 200 includes a temperature sensor 240 or sensors and a control box 250 which are added to control the amplitude of the electric field generated so not to generate excessive heating in the area that is treated.

The generator 210 generates multiple alternating voltage waveforms at frequencies in the range from about 50 KHz to about 500 KHz (preferably from about 100 KHz to about 300 KHz)(i.e., the TC fields) as instructed by a controller 300. Preferably, the controller 300 is a programmable unit, such as a personal computer or the like, that permits the user to input certain parameters and the controller 300 will then make the necessary computations. The controller 300 also distributes to each electrode 230 the designated potential wave. The required voltages are such the electric field intensity in the tissue to be treated is in the range of about 0.1V/cm, according to one exemplary embodiment, to about 10V/cm while in the other areas it is significantly lower.

When the control box 250 is included, it controls the outputs of the generator 210 so that they will remain constant at the values preset by the user or the control box 250. The controller 300 issues a warning or the like when the temperature (sensed by temperature sensor 240) exceeds a preset limit.

Figure 6:
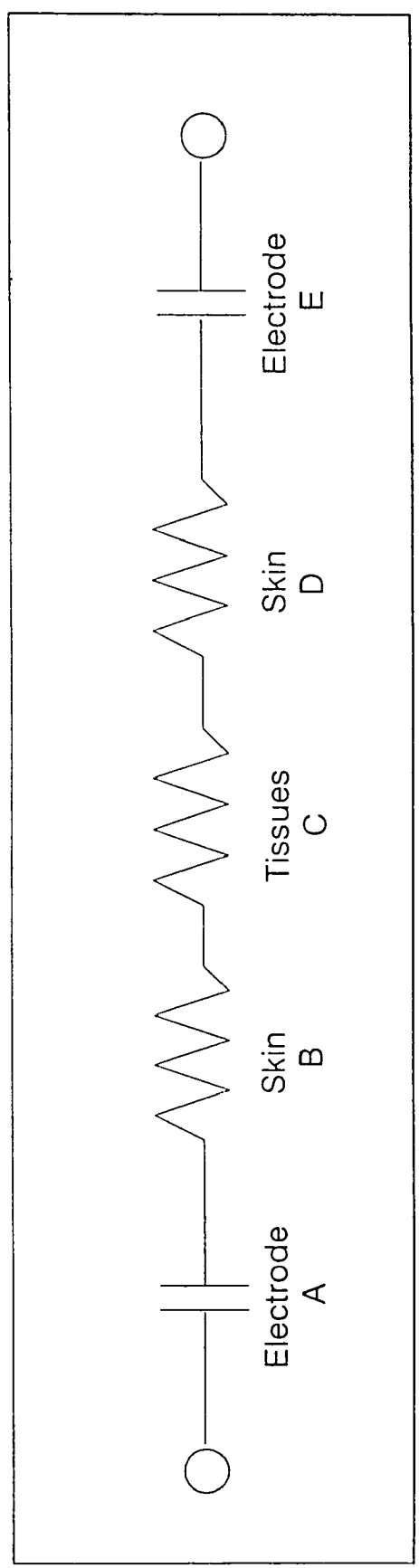
FIG. 6 is a simplified schematic diagram of an equivalent electric circuit of insulated electrodes of the apparatus of FIG. 5.

The details of the construction of the isolects 230 is based on their electric behavior that can be understood from their simplified electric circuit when in contact with tissue as generally illustrated in FIG. 6. In the illustrated arrangement, the potential drop or the electric field distribution between the different components is determined by their relative electric impedance, i.e., the fraction of the field on each component is given by the value of its impedance divided by the total circuit impedance. For example, the potential drop on element $\Delta V_A = A/(A+B+C+D+E)$. Thus, for DC or low frequency AC, practically all the potential drop is on the capacitor (that acts as an insulator). For relatively very high frequencies, the capacitor practically is a short and therefore, practically all the field is distributed in the tissues. At the frequencies of the present TC fields (e.g., 50 KHz to 500 KHz), which are intermediate frequencies, the impedance of the capacitance of the capacitors is dominant and determines the field distribution. Therefore, in order to increase the effective voltage drop across the tissues (field intensity), the impedance of the capacitors is to be decreased (i.e., increase their capacitance). This can be achieved by increasing the effective area of the "plates" of the capacitor, decrease the thickness of the dielectric or use a dielectric with high dielectric constant.

In order to optimize the field distribution, the isolects 230 are configured differently depending upon the application in which the isolects 230 are to be used. There are two principle modes for applying the present electric fields (TC fields). First, the TC fields can be applied by external isolects and second, the TC fields can be applied by internal isolects.

Since the thin insulating layer can be very vulnerable, etc., the insulation can be replaced by very high dielectric constant insulating materials, such as titanium dioxide (e.g., rutil), the dielectric constant can reach values of about 200. There a number of different materials that are suitable for use in the intended application and have high dielectric constants. For example, some materials include: lithium nibate ($LiNbO_3$), which is a ferroelectric crystal and has a number of applications in optical, pyroelectric and piezo-electric devices; yttrium iron garnet (YIG) is a ferrimagnetic crystal and magneto-optical devices, e.g., optical isolator can be realized from this material; barium titanate ($BaTiO_3$) is a ferromagnetic crystal with a large electro-optic effect; potassium tantalate ($KTaO_3$) which is a dielectric crystal (ferroelectric at low temperature) and has very low microwave loss and tunability of dielectric constant at low temperature; and lithium tantalate ($LiTaO_3$) which is a ferroelectric crystal with similar properties as lithium niobate and has utility in electro-optical, pyroelectric and piezoelectric devices. It will be understood that the aforementioned exemplary materials can be used in combination with the present device where it is desired to use a material having a high dielectric constant.

One must also consider another factor that effects the effective capacity of the isolects 230, namely the presence of air between the isolects 230 and the skin. Such presence, which is not easy to prevent, introduces a layer of an insulator with a dielectric constant of 1.0, a factor that significantly lowers the effective capacity of the isolects 230 and neutralizes the advantages of the titanium dioxide (routil), etc. To overcome this problem, the isolects 230 can be shaped so as to conform with the body structure and/or (2) an intervening filler 270 (as illustrated in FIG. 22C), such as a gel, that has high conductance and a high effective dielectric constant, can be added to the structure. The shaping can be pre-structured (see FIG. 22A) or the system can be made sufficiently flexible so that shaping of the isolects 230 is readily achievable. The gel can be made of hydrogels, gelatins, agar, etc., and can have salts dissolved in it to increase its conductivity. The exact thickness of the gel is not important so long as it is of sufficient thickness that the gel layer does not dry out during the treatment. In one exemplary embodiment, the thickness of the gel is about 0.5 mm to about 2 mm.

In order to avoid overheating of the treated tissues, a selection of materials and field parameters is needed. The isolects insulating material should have minimal dielectric losses at the frequency ranges to be used during the treatment process. This factor can be taken into consideration when choosing the particular frequencies for the treatment. The direct heating of the tissues will most likely be dominated by the heating due to current flow (given by the I*R product). However, dielectric losses can also contribute and in addition, the isolect (insulated electrode) 230 and its surroundings should be made of materials that facilitate heat losses and its general structure should also facilitate head losses, i.e., minimal structures that block heat dissipation to the surroundings (air) as well as high heat conductivity.

As previously mentioned, a coupling agent, such as a conductive gel, is preferably used to ensure that an effective conductive environment is provided between the insulated electrode 230 and the skin surface 231. The coupling agent is disposed on the insulated electrode 230 and preferably, a uniform layer of the agent is provided along the surface of the electrode 230. One of the reasons that the units 540 need replacement at periodic times is that the coupling agent needs to be replaced and/or replenished. In other words, after a predetermined time period or after a number of uses, the patient removes the units 540 so that the coupling agent can be applied again to the electrode 230.

The leads 220 are standard isolated conductors with a flexible metal shield, preferably grounded so that it prevents the spread of the electric field generated by the leads 220. The isolects 230 have specific shapes and positioning so as to generate an electric field of the desired configuration, direction and intensity at the target volume and only there so as to focus the treatment. The generation of electric field distribution of the desired characteristics is achieved by placement of numerous isolects on the body surface, and when necessary also inside the body. The number of electrodes 230 can typically be about 20–100, placed about 4–12 cm apart. The electrodes 230 can be positioned individually on the skin, etc., (as by an adhesive), or be part of an article of clothing, such as elastic undershirt, as illustrated in FIGS. 8–9, that holds the electrodes in place. Each isolect 230 (electrode) is connected to the controller 300 and is provided with a voltage signal the amplitude and shape of which was calculated specifically for the particular electrode. One will also appreciate that the calculation for the voltage signal (amplitude and shape) can be made for groups of isolects as well instead of for individual isolects.

According to one aspect, a method for optimizing the selective destruction of dividing cells is provided and the method includes the general steps of calculating the spatial and temporal distribution of electric fields for optimal treatment of a specific patient that has a tumor of specific characteristics. This calculation takes into consideration the location and the specific characteristics of the tumor.

Figure 7:
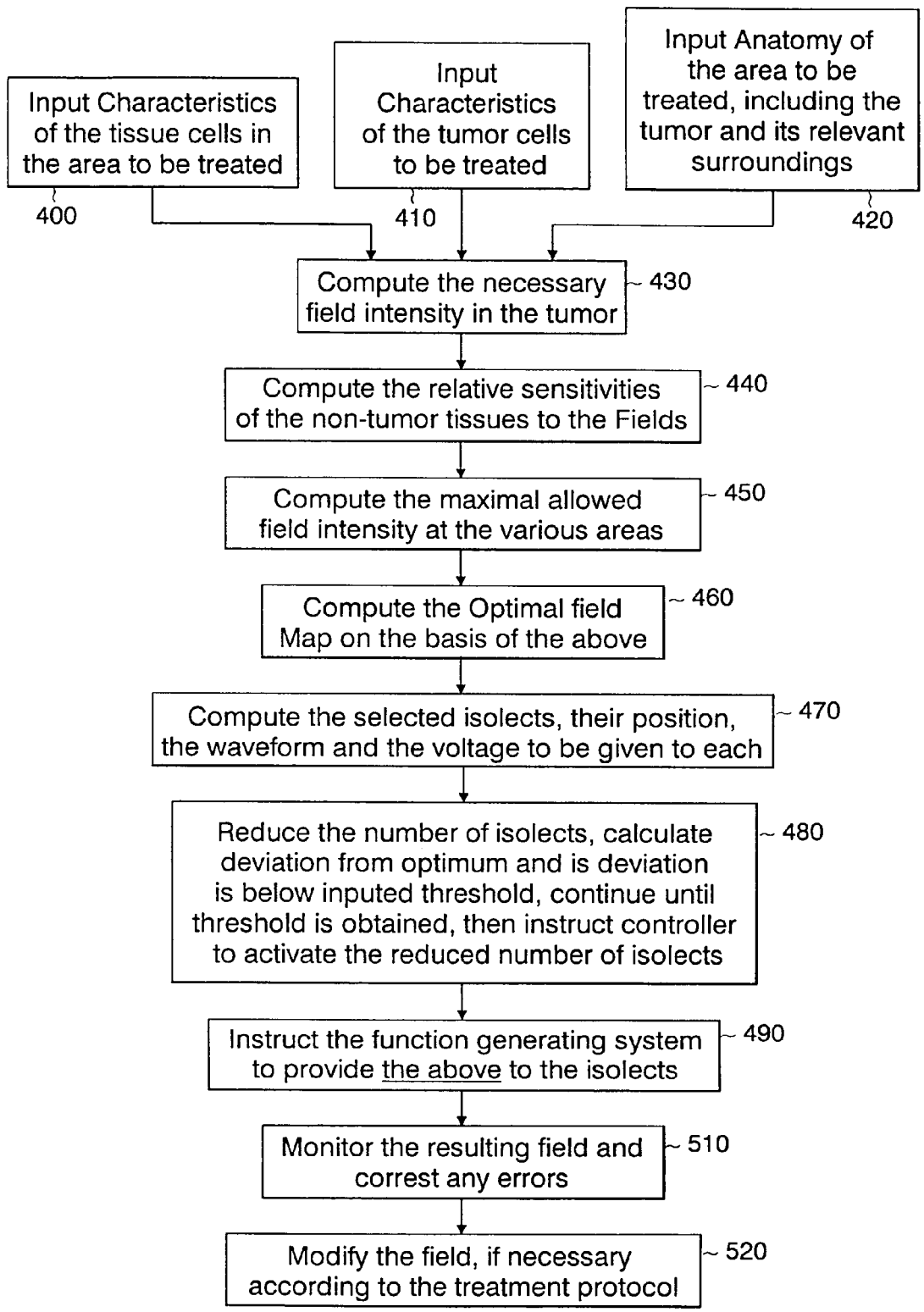
FIG. 7 is diagrammatic flow chart for computing an optimal electric field.

One exemplary process for computing and applying an optimal electric field is described with reference to the flow chart of FIG. 7. FIG. 7 thus gives a general overview of the present optimization process. In steps 400, 410, 420, the user inputs different types of information that is used to compute the optimal electric field. For example, at step 400, the user inputs characteristics of the tissue cells in the area to be treated; at step 410, the user inputs characteristics of the tumor cells to be treated; and at step 420, the user inputs the anatomy of the area to be treated, including the tumor and its relevant surroundings. At step 430, this inputted information is used to compute the necessary field intensity in the tumor. The relative sensitivities of the non-tumor tissues to the electric fields is computed in step 440. At step 450, the maximal allowed field intensity at the various areas is determined and then based on the information inputted in steps 400 through 450, an optimal field map is computed at step 460. At step 470, the selected isolects (those present in the optimal field map) are computed as well as their position and waveform and the voltage that is to be delivered to each isolect. In order to further minimize the field map, the number of isolects is preferably reduced in step 480 to produce a modified field map and then the deviation of the modified map from the optimum is calculated. The calculated deviation is then compared to an inputted threshold value and if the calculated deviation is below the inputted threshold, the process of reducing the number of isolects is continued until the inputted threshold is obtained. Once the inputted threshold is obtained, a signal is delivered to the controller to activate the reduced number of isolects. At step 490, a signal is generated and delivered to the function generating system (e.g., the generator that produces the waveforms mentioned in step 470, such as an analog wave generator or a digital one, e.g., a waveform generated by a PC and outputted through a digital to analog converter) or the system is otherwise instructed to provide the selected waveform and voltage to the isolects. The field that results from activation of the isolects is monitored at step 510 and any errors are corrected. If any errors or abnormalities are detected, the field is modified as necessary according to the treatment protocol at step 520. The various algorithms that are used for the necessary computations are described hereinafter.

Since the signal that is delivered to each electrode (isolect) is a voltage signal that has been specifically created for the specific electrode or for a specific group of electrodes, the calculation of this voltage signal is an important aspect of the present invention.

The voltages for the isolects are calculated as follows. Following the anatomical definition of the areas to be treated, taking into consideration the specific sensitivity of the different tissues to the TC fields and the target area, the desired field distribution map is constructed, as described in the flow chart of FIG. 7. The processor, which was fed the coordinates of all available isolects, now computes the vector sum of the fields generated by each isolect at each point in time. The computation can be made significantly faster in cases where an analytical expression for the electric field originating from arbitrary placed electrodes is available. Such a computation can be performed, for example, for the simple case; an isolect placed on a muscle, or similar tissue, for which an analytical expression for the electric field is:

$$E = \frac{V}{r \ln\left(\frac{R_2}{R_1}\right)} \frac{\varepsilon_{coat}}{\varepsilon_{muscle}}$$

Where $R_1$ is the radius of the metallic part of the isolect, $R_2$ is the isolect radius including coating $\varepsilon_{coat}$ and $\varepsilon_{muscle}$ are the dielectric constants of the isolect coating and muscle, respectively and r is the distance between the electrodes to the point where one wants to calculate the field. The fields generated in more complex systems are usually computed by finite element methods, as described below.

Using this analytical expression, a series of iterations is initiated and the controller 300, more specifically the CPU thereof, calculates the TC field, using optimization methods, to optimize the voltage and the position of each electrode so that one gets the desired spatial arrangement of the electric field. The computation begins with a set of isolect locations and initial conditions, chosen arbitrary, or based on a set of assumptions or previous experience. The field maps thus generated are compared with the reference optimal map that was generated, as described in the flow chart illustrated in FIG. 7. In the subsequent iterations, the voltage and the position of the different isolects are changed and an optimal fit with the optimal map is sought. In other words, one optimizes the correlation between the calculated electric field (TC field) and the desired electric field (TC field). In the above optimization method one can use, for example, the robust numeric optimization method, known as the Nelder-Mead simplex method, as described in Neider and Mead, Computer Journal Vol. 7, p. 308 (1965); Lagarias, J. C., J. A. Reeds, M. H. Wright and P. E. Wright "Convergence Properties of the Neider-Mead Simplex Method in Low Dimensions", SIAM Journal of Optimization, Vol. 9, Number 1, pp. 112–147, 1986, all of which are hereby incorporated by reference in their entirety. In addition, the calculations of the optimization method include the method "Sequential Quadratic Programming", and this method is intended for checking that the first one went fine. The references include Fletcher, R. and M. J. D. Powell, "A Rapid Convergent Descent Method for Minimization," Computer Journal, Vol. 6, pp. 163–168; and Goldfarb, D., "A Family of Variable Metric Updates Derived by Variational Means:," Mathematics of Computing, Vol. 24, pp. 23–26, 1970, all of which are hereby incorporated by reference in their entirety.

Now referring to FIGS. 8–9 in which an article of clothing 600 in the form of an undershirt is shown. Depending upon the precise location of the tumor (target tissue), the undershirt 600 can be of an oversized type in that, as illustrated, the undershirt 600 extends below the waist of the patient and in fact, it protrudes around a portion of the user's upper legs (thighs); however, it will be appreciated that the undershirt 600 can be of a more conventional type that lies above the waist. The undershirt 600 has a predetermined number of electrodes 230 (e.g., 20–100 in number) that are arranged either in an orderly manner as shown (rows and columns) or they can be arranged in a irregular pattern depending upon where the optimal positioning of the electrodes 230 is determined to be. The electrodes 230 are held in place by the undershirt construction, e.g., by adhesives or by stitching, etc. As shown in FIG. 9, the electrodes 230 completely extend radially around the body of the patient.

Figure 10:
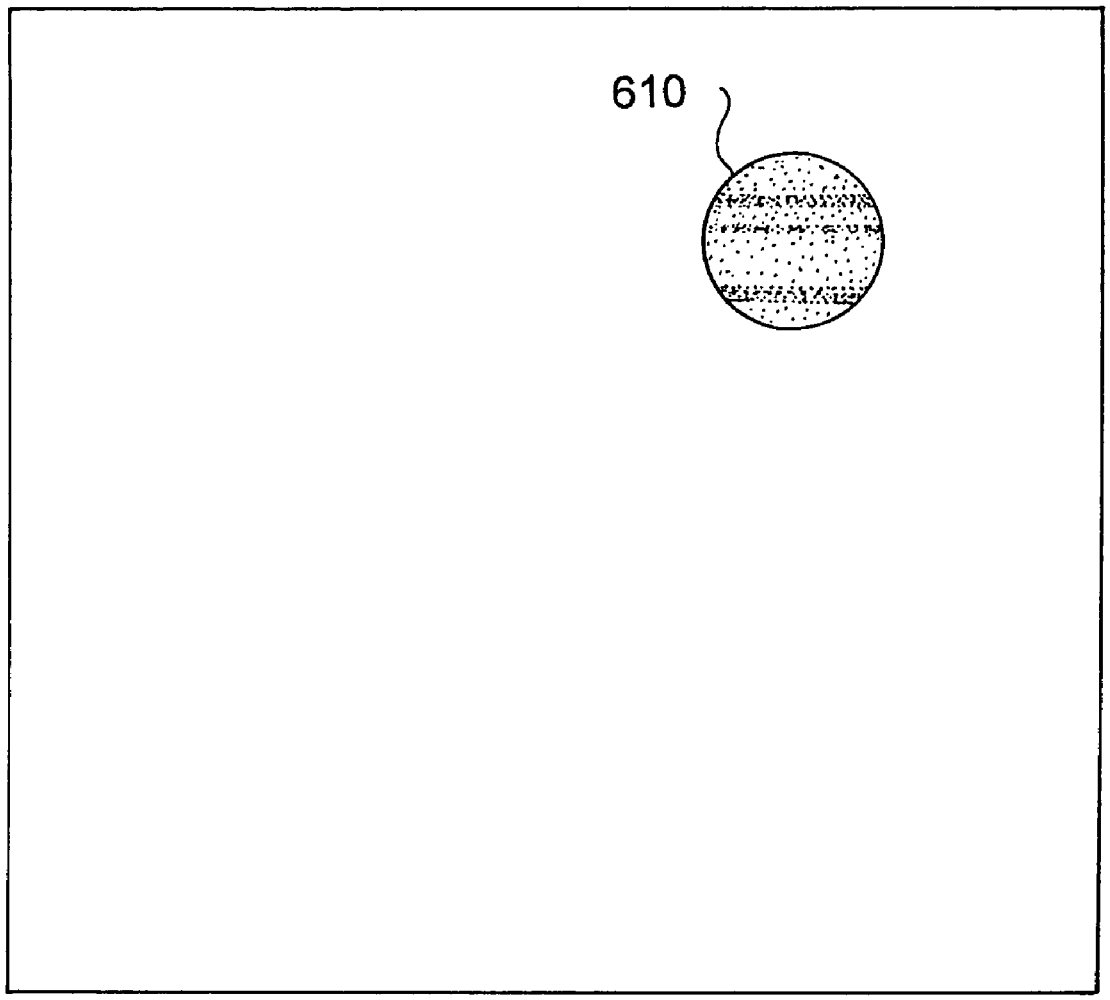
FIG. 10 is schematic view of a target area on which the electric field is to be focused.

In FIG. 10, this type of procedure was carried out with the aim to effectively focus the field at the selected area, which in this Figure is denoted by the circle 610. In this example, random initialization of the electrode voltage and positions were used.

Figure 11:
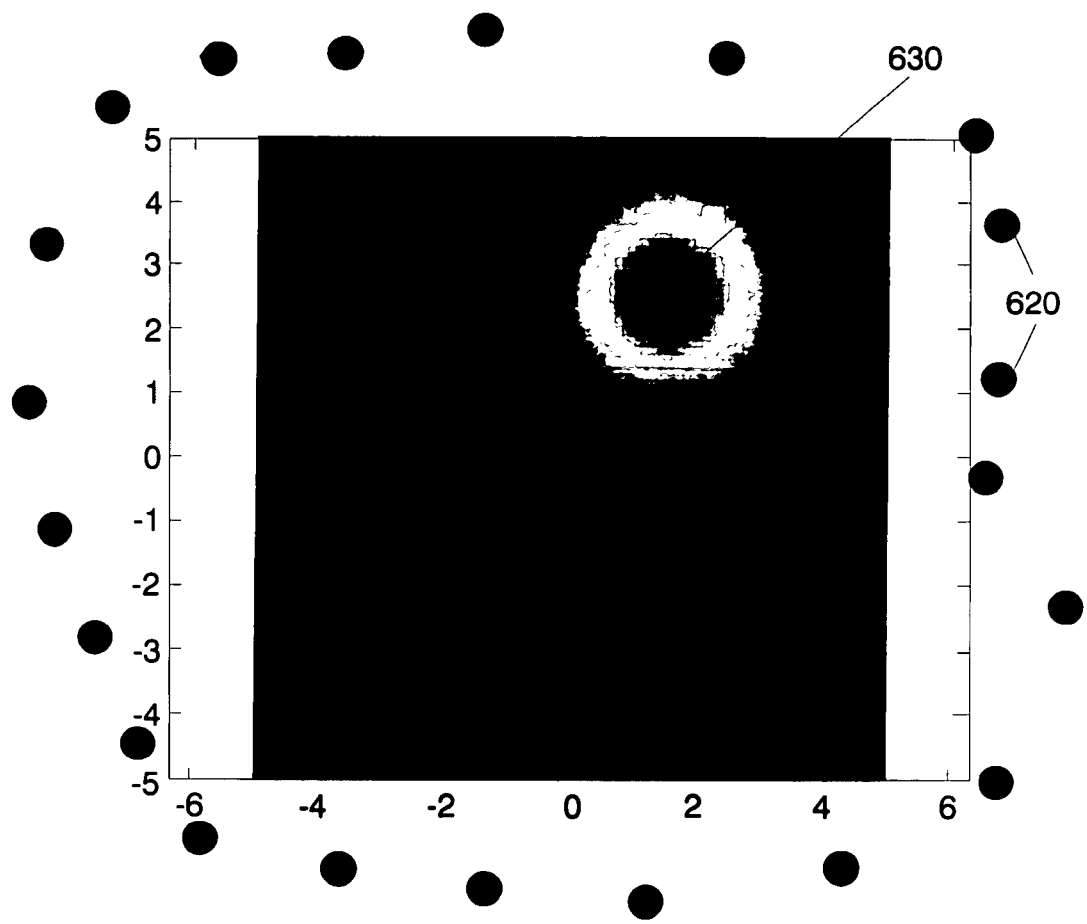
FIG. 11 is a photographic image of the optimal position of electrodes around the target area (tissue mass) of FIG. 10.

In FIG. 11, the calculated optimal position of the electrodes, depicted by circles 620, is illustrated around the tissue mass 630 where the electric field (TC field) intensity is minimal, as denoted by 640, while the intensity of the electric field increases in the vicinity of the target (tissue mass) 630.

Figure 12:
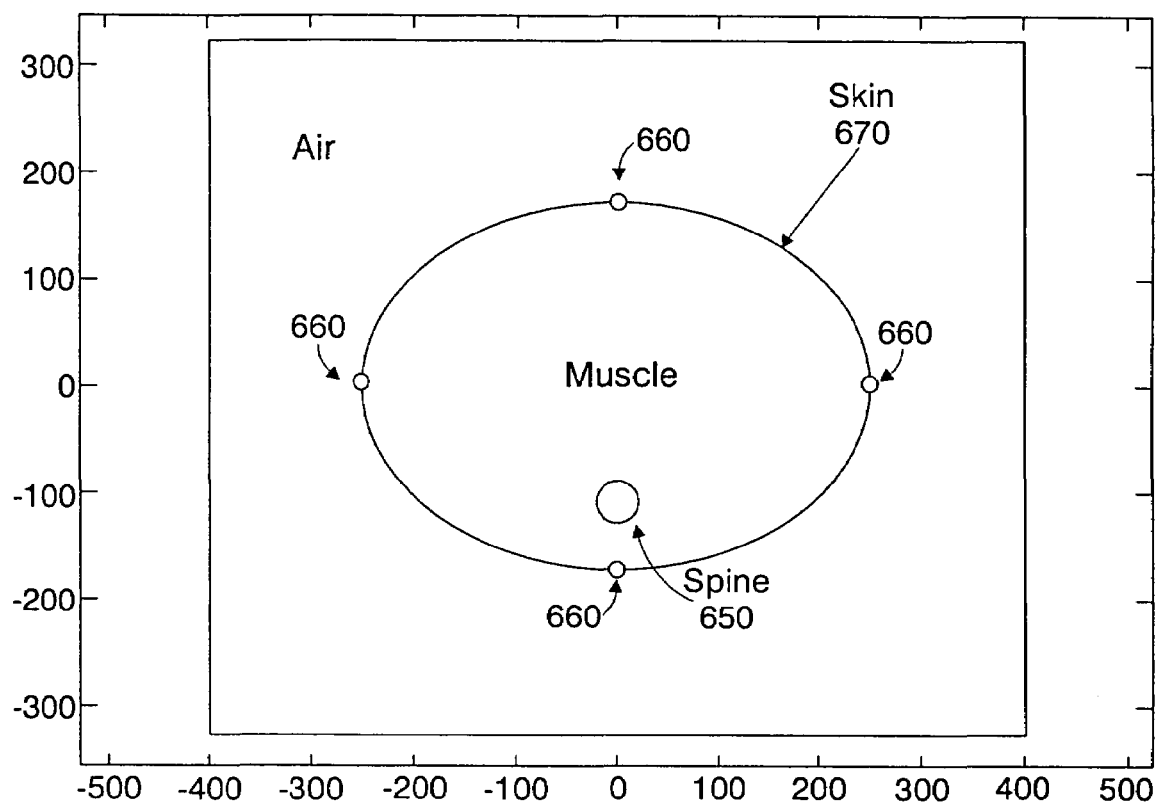
FIG. 12 is a schematic illustration of a geometric model for positioning electrodes around a spine of a human patient where the electrodes are arranged symmetrically.

In yet another example of the procedure of calculating the isolect placement that would give high field intensity at a number of skin locations, for treatment of malignant melanoma's while having minimal field at the spine is illustrated and described with reference to FIGS. 12–18. In this example, one will appreciate how the anatomy, the isolect structure and the tissue electric characteristics are incorporated into the calculations. One of the advantages of using an electric field to repress the prosperity of cells is that areas inside a human being can be left outside of the electric field influence. According to this one example, a model is constructed for a human having four electrodes around the mid body portion and the electrodes are specifically arranged so that the electric field around the human's spine is zero. The calculations are based on finite element mesh (FEM) and the geometric model is described and illustrated with reference to FIG. 12. In FIG. 12, the axis units are in millimeters and the body is 0.5 m width with a 0.35 thickness. FIG. 12 shows the location of the spine 650 relative to four electrodes 660 that are spaced therearound. A skin boundary or layer of the patient is generally shown at 670 with muscle 680 being shown as occupying the area within the skin boundary 670 and around the spine 650.

Figure 13:
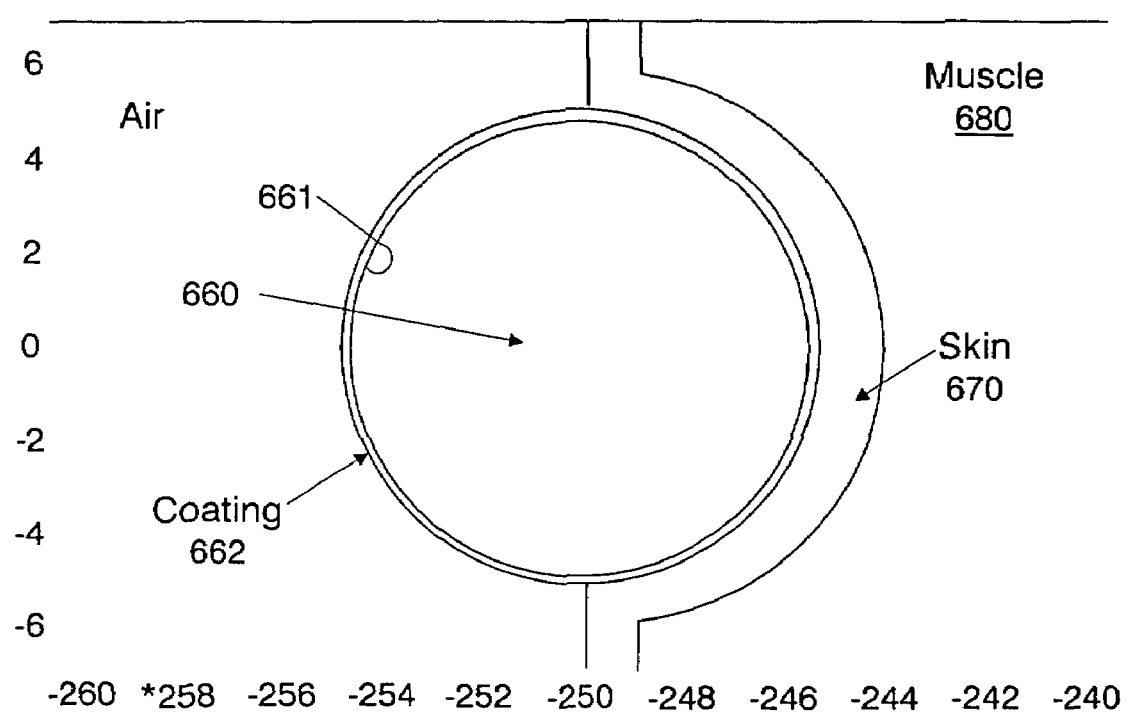
FIG. 13 is an enlarged schematic illustration of one electrode of the arrangement of FIG. 12.

FIG. 13 is also a geometric model illustrating an enlargement of the area around one electrode 670 of FIG. 12 showing the interaction between the electrode 670 and the skin layer 670. The axis units in FIG. 13 are in millimeters and in this exemplary embodiment, the electrode 660 includes a coating 662 that is formed of PVC or potassium tantalate. In this example, the electrode 660 has a diameter of about 10 mm and the coating 662 that is disposed around an outer surface 661 thereof has a thickness of about 0.1 mm. The skin layer 670 has a thickness of about 1 mm. Table 1 sets forth the parameters for the materials that are used in the calculations that are used with the geometric models of FIGS. 12 and 13.

TABLE 1

| Material Data | | |
|---|---|---|
| Dielectric medium | Dielectric Constant | Conductivity (S/m) |
| Air | 1 | 0 |
| PVC Coating | 2.6 | 0 |
| Muscle | 8089 | 0.36 |
| Skin | 1119 | 0.00045 |
| Spine | 227 | 0.0208 |

In all of the calculations for this example, the voltage between the electrodes 660 was 1V and the frequency of the sine voltage was 100 KHz.

Figure 14:
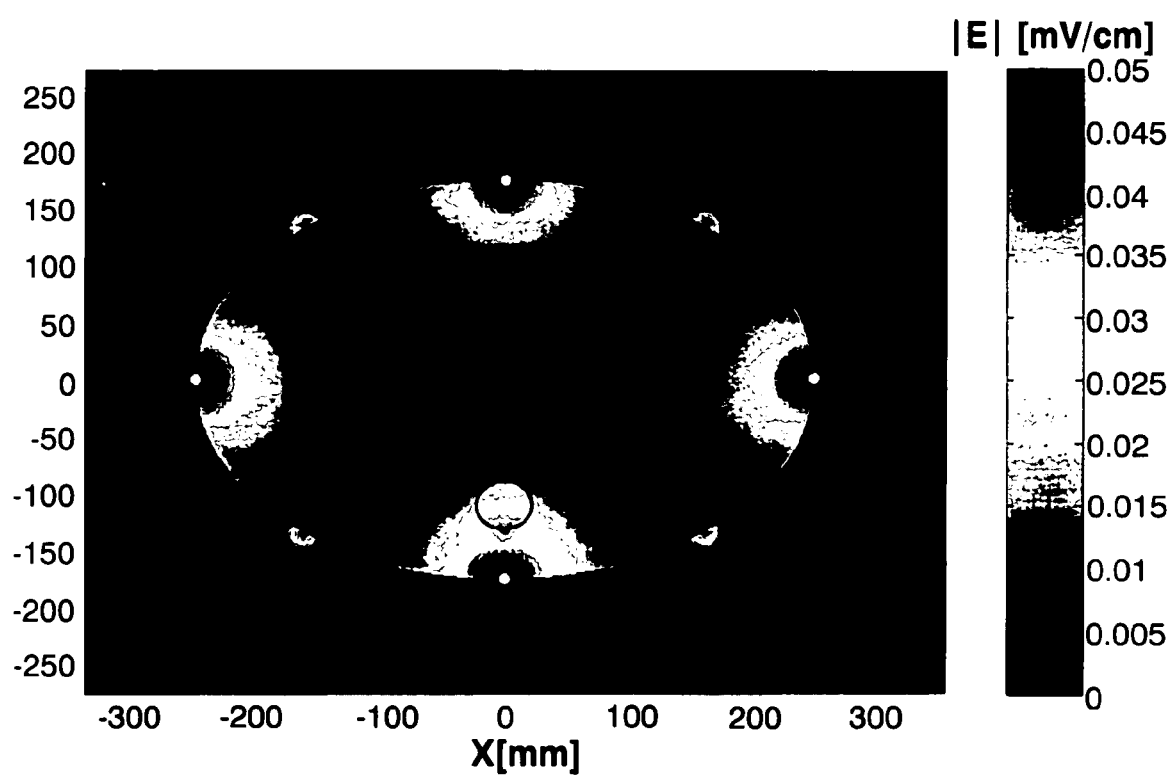
FIG. 14 is a photographic image of a resulting electric field generated when the electrodes are arranged symmetrically as illustrated in FIG. 12.
Figure 15:
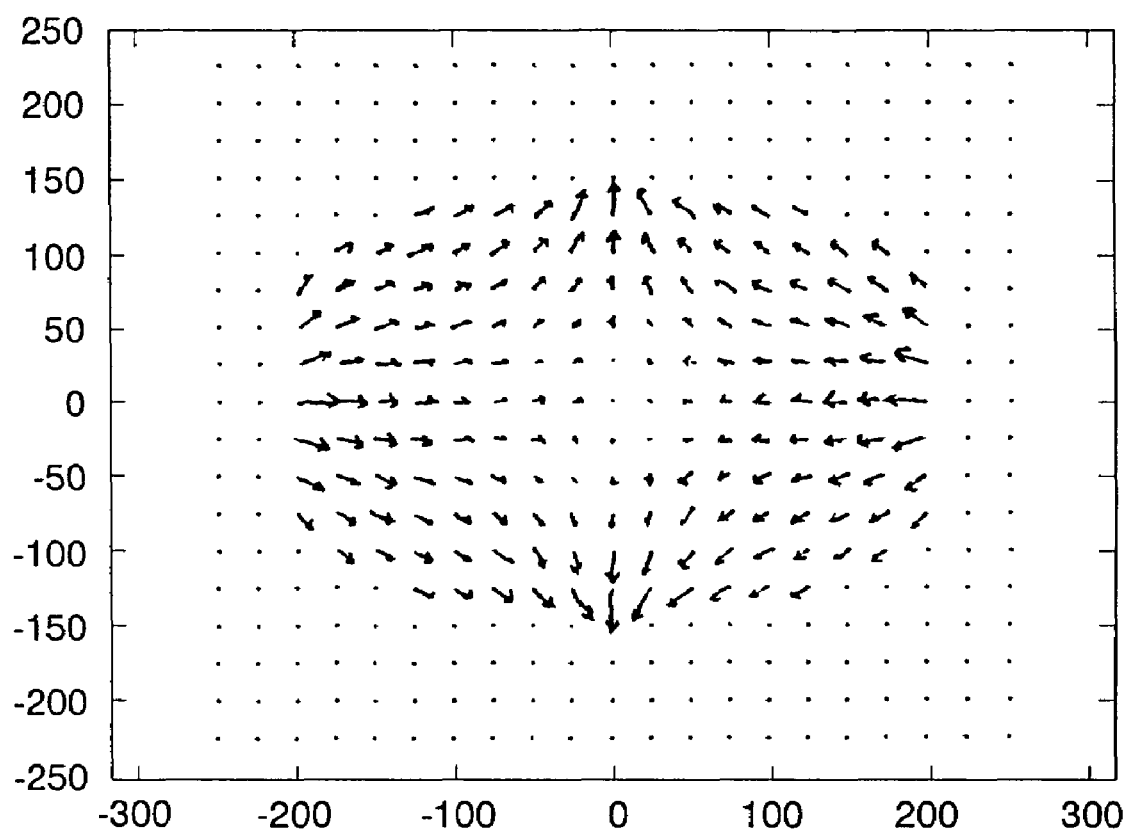
FIG. 15 is a schematic illustration representing the electric field of FIG. 14 by arrows.
Figure 16:
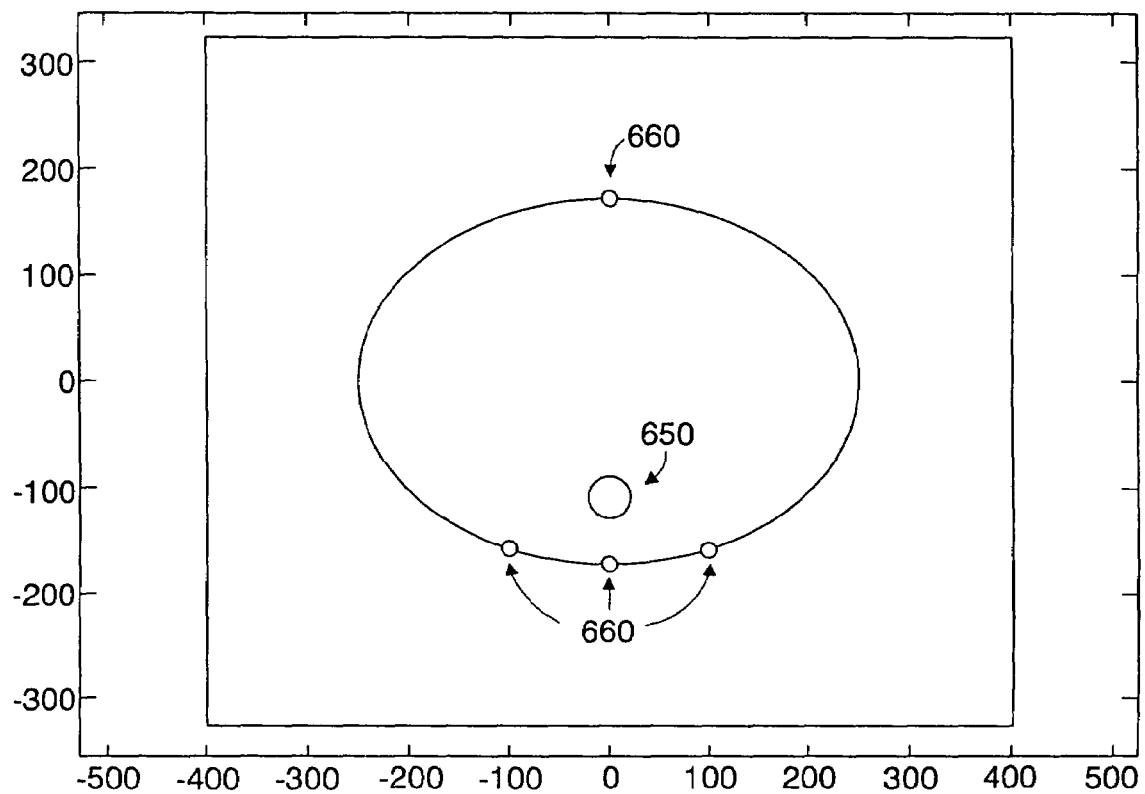
FIG. 16 is a schematic illustration of a geometric model for positioning electrodes around the spine in an asymmetric manner so that the electric field in the area of the spine is zero.
Figure 17:
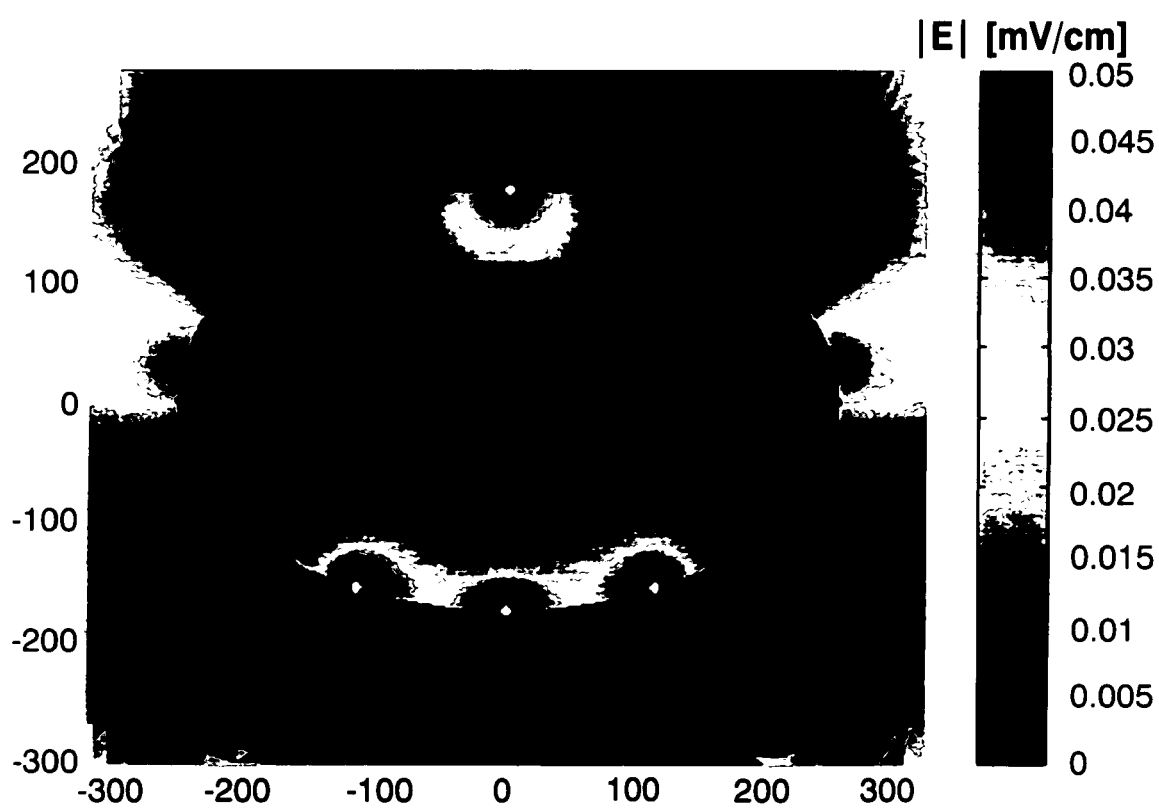
FIG. 17 is a photographic image of a resulting electric field generated when the electrodes are arranged asymmetrically as illustrated in FIG. 16.
Figure 18:
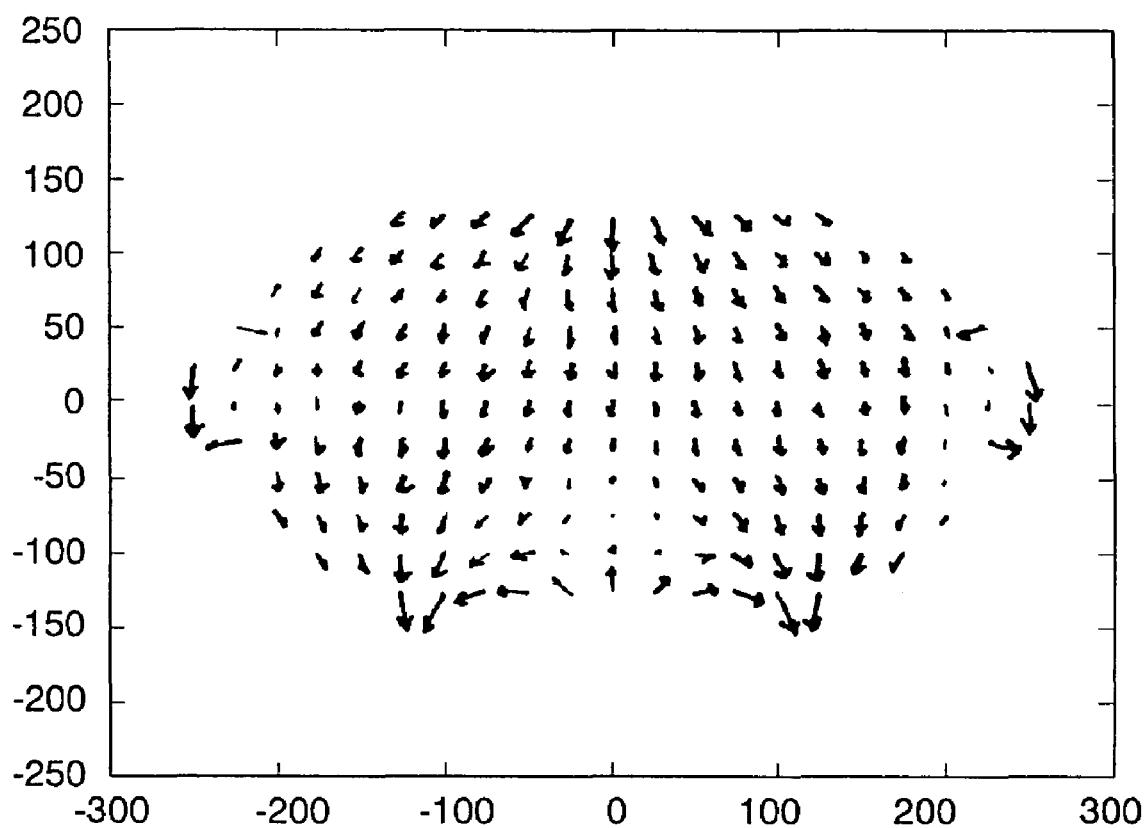
FIG. 18 is a schematic illustration representing the electric field of FIG. 17 by arrows.

In this example, the electrodes 660 are placed in a symmetric formation such that the electric field in the middle of the body is zero. FIG. 14 is photographic image of the electrodes 660 around the spine 650 illustrating the electric field representation in the symmetric formation of the electrodes. FIG. 15 is another representation of the electric field; however, this representation of the electric field is by arrows. As will be appreciated, only the electric field inside the body is shown. As can be seen from both FIGS. 14 and 15, the electric field is zero in the middle of the body and is very high in the area of the spine 650. This is unwanted since the presence of the electric field near the spine 650 can be potentially harmful. In FIG. 16, the electrodes 660 have been rearranged so that the electric field is zero in the spine area 650 and not zero in the middle of the body. FIG. 16 is a schematic illustration of the arrangement of the electrodes 660 that causes a zero electric field in the area of the spine 650. FIG. 17 is a photographic image of the electric field in an asymmetric formation of the electrodes and FIG. 18 is another representation of the electric field, similar to FIG. 15, in which the electric field is represented by arrows and only the electric field inside the body is drawn. As can be seen from FIGS. 17 and 18, the asymmetric arrangement of the electrodes causes a zero electric field in the area of the spine 650, while the field outside the spine 650 is not zero.

Based on the above calculations, one will appreciate that a proper arrangement of the electrodes can shape the electric field so that it becomes zero at areas we choose, such as the spine area 650, in this example. In application, the procedure can entail using a CT image to position the internal organs, calculate on-line the electric field using the present methodology and automatically position the electrodes on the patient's body so that an area that we do not want to harm will not suffer from the presence of an electric field.

The specifications of the apparatus 200 as a whole and its individual components are largely influenced by the fact that at the frequency of the present TC fields (50 KHz–500 KHz), living systems behave according to their "Ohmic", rather than their dielectric properties. The only elements in the apparatus 200 that behave differently are the insulators of the isolects 230 (see FIGS. 19–21). The isolects 200 consist of a conductor in contact with a dielectric that is in contact with the conductive tissue thus forming a capacitor.

Figure 19:
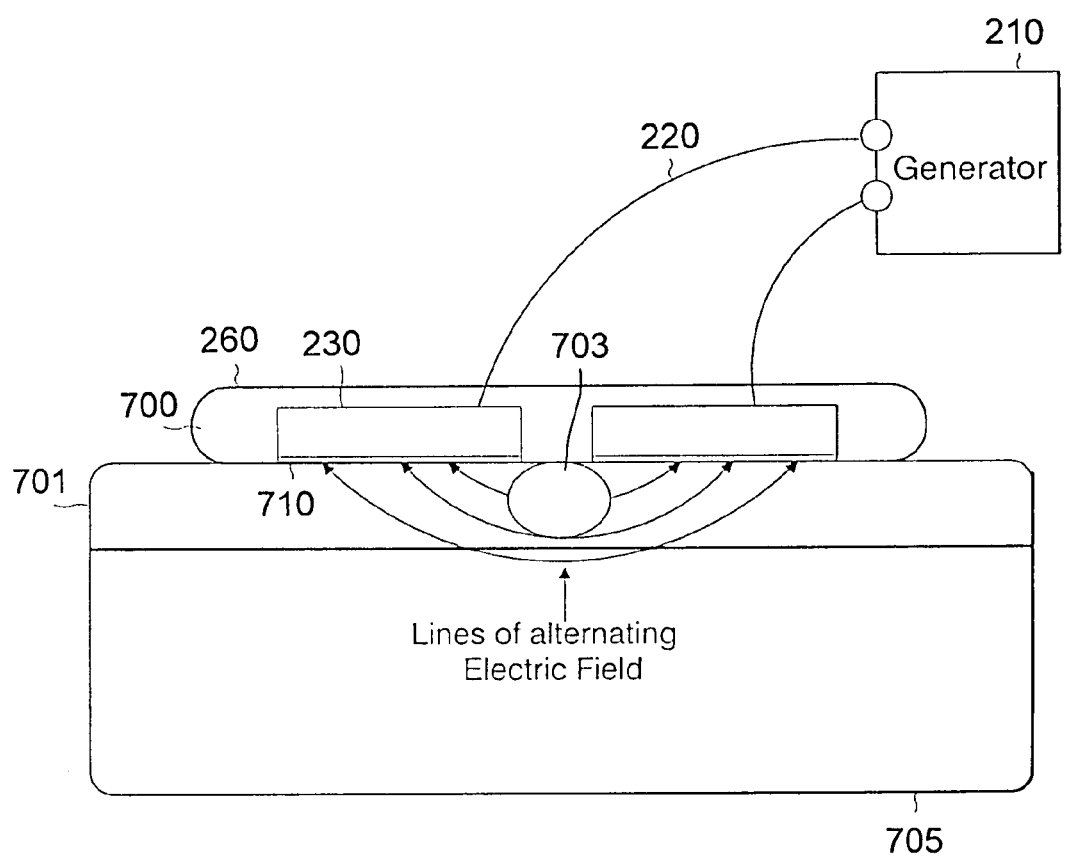

There are any number of different types of applications in which the apparatus 200 or one of the others disclosed herein can be used. The following applications are merely exemplary and not limiting of the number of different types of applications which can be used. FIG. 19 illustrates an exemplary embodiment where the isolects 230 are incorporated in a skin patch 700. The skin patch 700 can be a self-adhesive flexible patch with one or more pairs of isolects 230. The patch 700 includes internal insulation 710 (formed of a dielectric material) and the external insulation 260 and is applied to skin surface 701 that contains a tumor 703 either on the skin surface 701 or slightly below the skin surface 701. Tissue is generally indicated at 705. To prevent the potential drop across the internal insulation 710 to dominate the system, the internal insulation 710 must have a relatively high capacity. This can be achieved by a large surface area; however, this may not be desired as it will result in the spread of the field over a large area (e.g., an area larger than required to treat the tumor). Alternatively, the internal insulation 710 can be made very thin and/or the internal insulation 710 can be of a high dielectric constant. As the skin resistance between the electrodes (labeled as A and E in FIG. 6) is normally significantly higher than that of the tissue (labeled as C in FIG. 6) underneath it (1–10 KΩ vs. 0.1–1 KΩ), most of the potential drop beyond the isolects occurs there. To accommodate for these impedances (Z), the characteristics of the internal insulation 710 (labeled as B and D in FIG. 6) should be such that they have impedance preferably under 100 KΩ at the frequencies of the present TC fields (e.g., 50 KHz to 500 KHz). For example, if it is desired for the impedance to be about 10 K Ohms or less, such that over 1% of the applied voltage falls on the tissues, for isolects with a surface area of 10 mm$^2$, at frequencies of 200 KHz, the capacity should be on the order of $10^{-10}$ F, which means that using standard insulations with a dielectric constant of 2–3, the thickness of the insulating layer 710 should be about 50–100 microns. An internal field 10 times stronger would be obtained with insulators with a dielectric constant of about 20–50.

Figure 20:
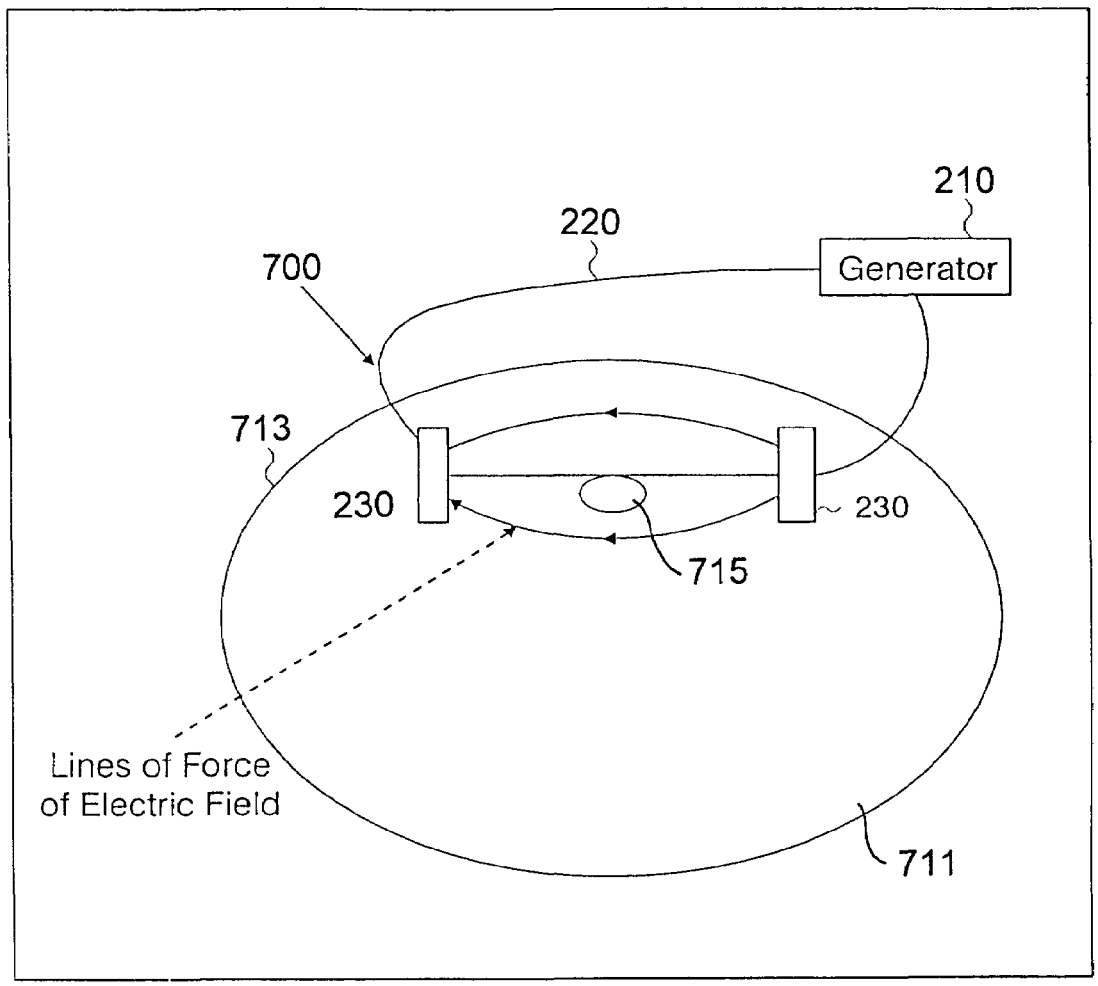
Figure 21:
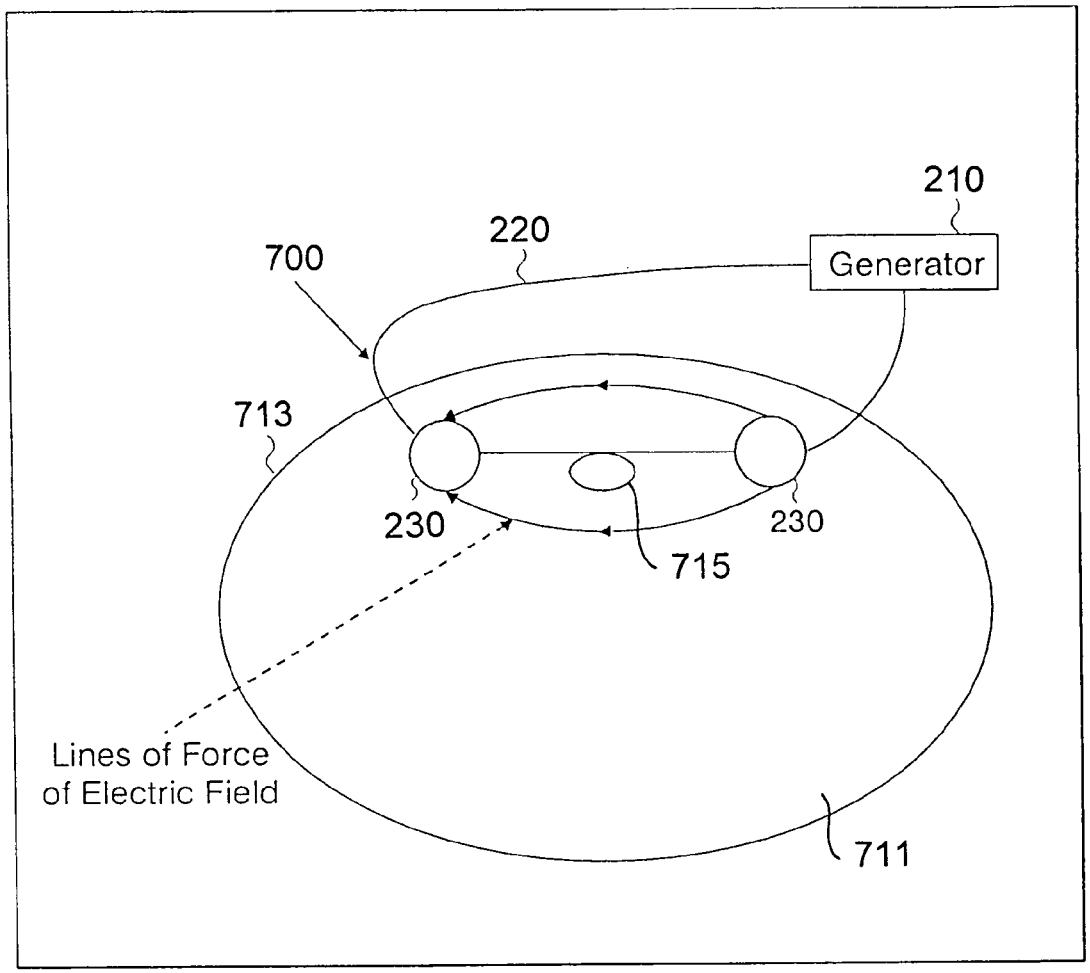
Figure 22:
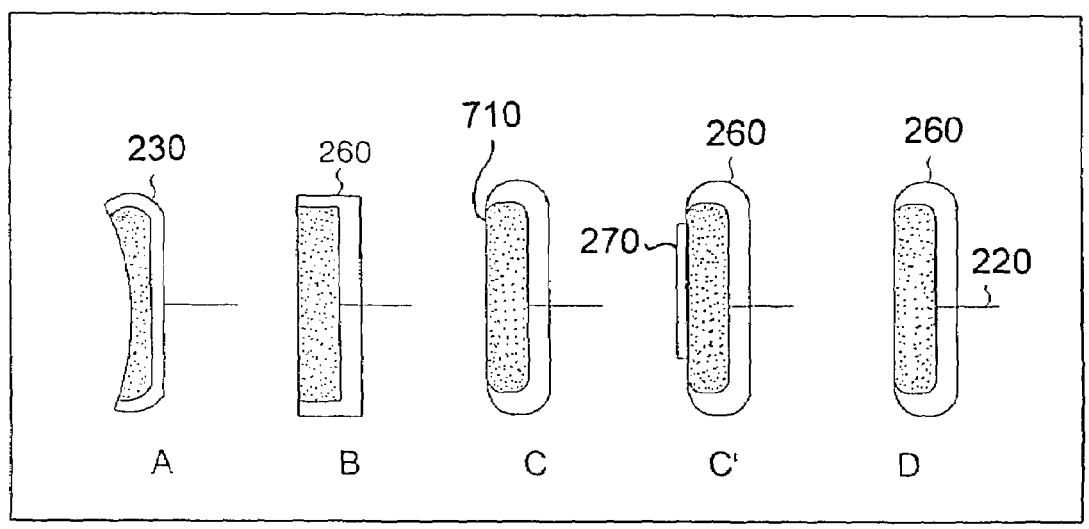
FIGS. 22A–22D are cross-sectional illustrations of various constructions of the insulated electrodes of FIG. 5.

FIGS. 20 and 21 illustrate a second type of treatment using the isolects 230, namely electric field generation by internal isolects 230. A body to which the isolects 230 are implanted is generally indicated at 711 and includes a skin surface 713 and a tumor 715. In this embodiment, the isolects 230 can have the shape of plates, wires or other shapes that can be inserted subcutaneously or a deeper location within the body 711 so as to generate an appropriate field at the target area (tumor 715). FIG. 22 illustrates the various constructions of the isolects 230, including the use of internal insulation 710, a filler or gel 270 and external insulation 260.

Figure 23:
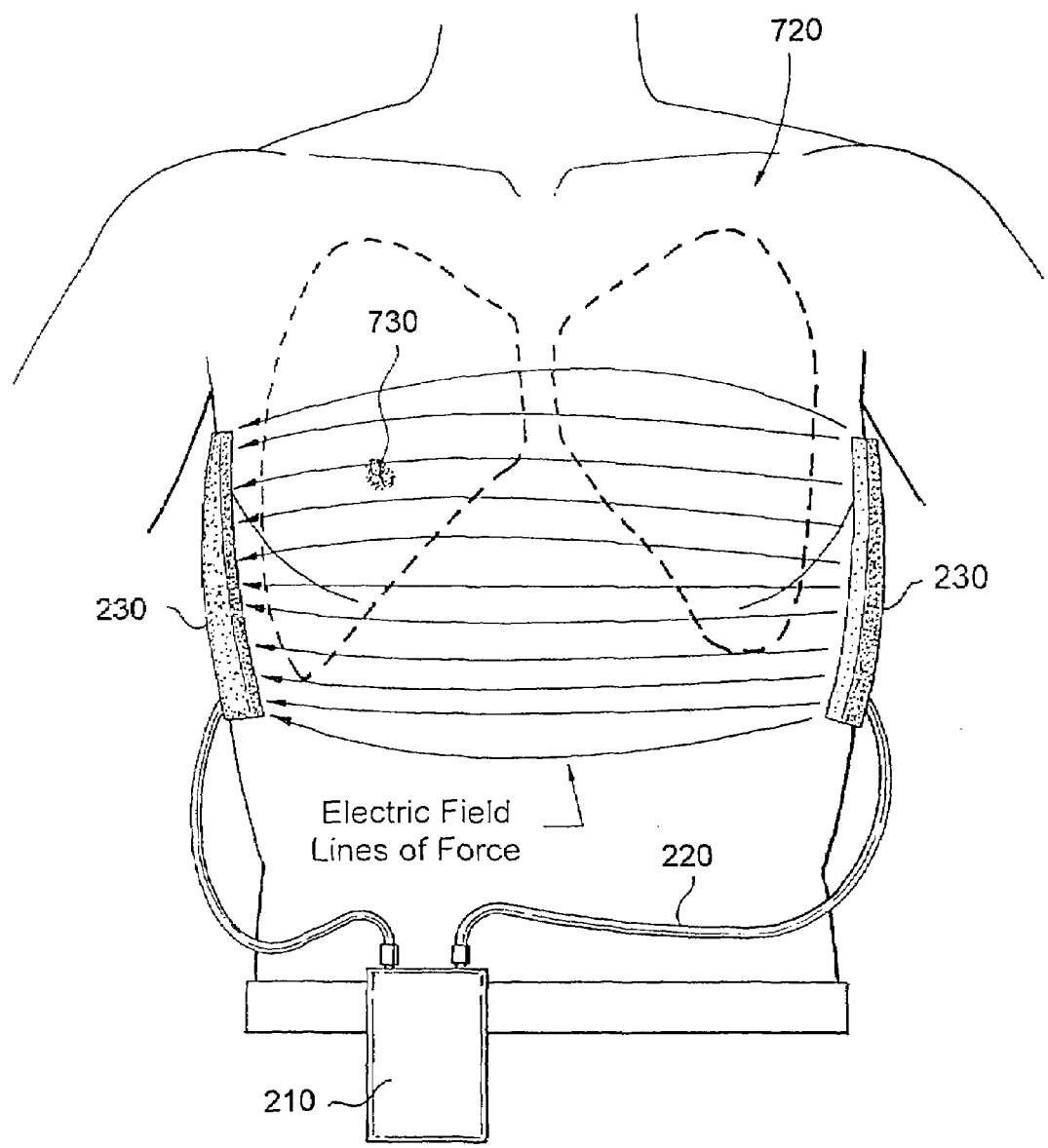
FIG. 23 is a front elevation view in partial cross-section of two insulated electrodes being arranged about a human torso for treatment of a tumor contained within the body, e.g., a tumor associated with lung cancer.

It will also be appreciated that the mode of isolects application is not restricted to the above descriptions. In the case of tumors in internal organs, for example, liver, lung, etc., the distance between each member of the pair of isolects 230 can be large. The pairs can even by positioned opposite sides of a torso 720, as illustrated in FIG. 23. The arrangement of the isolects 230 in FIG. 23 is particularly useful for treating a tumor 730 associated with lung cancer or gastrointestinal tumors. In this embodiment, the electric fields (TC fields) spread in a wide fraction of the body.

Figure 24:
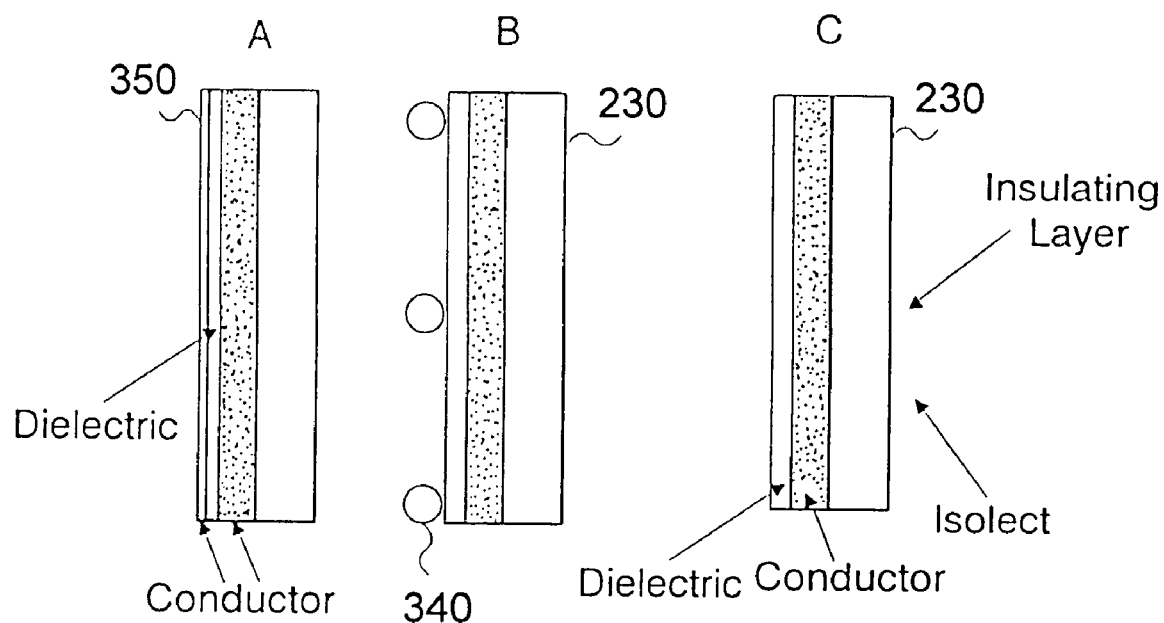
FIGS. 24A–24C are cross-sectional illustrations of various insulated electrodes with and without protective members formed as a part of the construction thereof.

In order to achieve the desirable features of the isolects 230, the dielectric coating of each should be very thin, for example from between 1–50 microns. Since the coating is so thin, the isolects 230 can easily be damaged mechanically. This problem can be overcome by adding a protective feature to the isolect's structure so as to provide desired protection from such damage. For example, the isolect 230 can be coated, for example, with a relatively loose net 340 that prevents access to the surface but has only a minor effect on the effective surface area of the isolect 230 (i.e., the capacity of the isolects 230 (cross section presented in FIG. 24B). The loose net 340 does not effect the capacity and ensures good contact with the skin, etc. The loose net 340 can be formed of a number of different materials; however, in one exemplary embodiment, the net 340 is formed of nylon, polyester, cotton, etc. Alternatively, a very thin conductive coating 350 can be applied to the dielectric portion (insulating layer) of the isolect 230. One exemplary conductive coating is formed of a metal and more particularly of gold. The thickness of the coating 350 depends upon the particular application and also on the type of material used to form the coating 350; however, when gold is used, the coating has a thickness from about 0.1 micron to about 0.1 mm.

In order to avoid overheating of the treated tissues, a selection of materials and field parameters is needed. The isolects insulating material should have minimal dielectric losses at the frequency ranges to be used during the treatment process. This factor can be taken into consideration when choosing the particular frequencies for the treatment. The direct heating of the tissues will most likely be dominated by the heating due to current flow (given by the I*R product). In addition, the isolect (insulated electrode) 230 and its surroundings should be made of materials that facilitate heat losses and its general structure should also facilitate head losses, i.e., minimal structures that block heat dissipation to the surroundings (air) as well as high heat conductivity.

Figure 25:
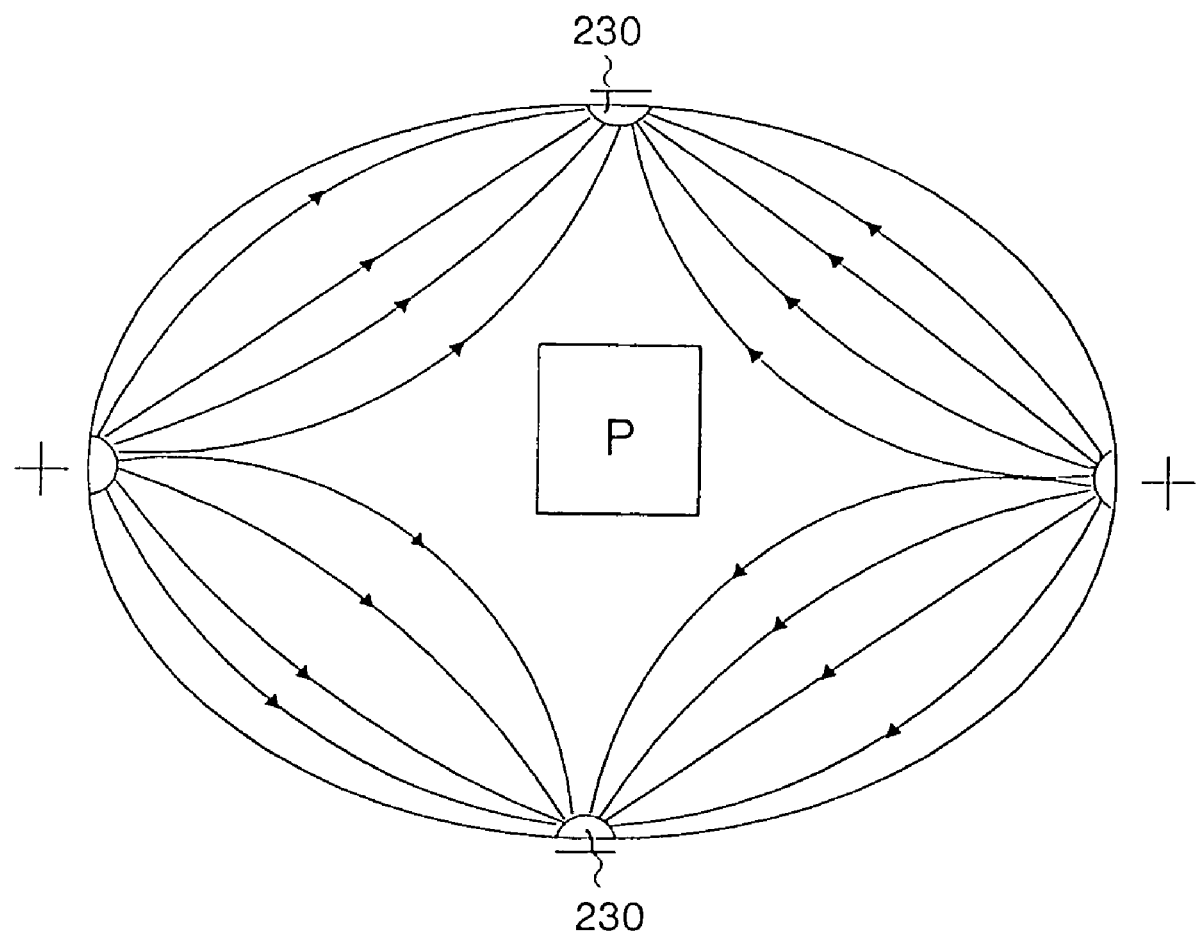
FIG. 25 is a schematic diagram of insulated electrodes that are arranged for focusing the electric field at a desired target while leaving other areas in low field density (i.e., protected areas)

The effectiveness of the treatment can be enhanced by an arrangement of isolects 230 that focuses the field at the desired target while leaving other sensitive areas in low field density (i.e., protected areas). The proper placement of the isolects 230 over the body can be maintained using any number of different techniques, including using a suitable piece of clothing that keeps the isolects at the appropriate positions. FIG. 25 illustrates such an arrangement in which an area labeled as "P" represents a protected area. The lines of field force do not penetrate this protected area and the field there is much smaller than near the isolects 230 where target areas can be located and treated well. In contrast, the field intensity near the four poles is very high.

The present inventor has thus uncovered that electric fields having particular properties can be used to destroy dividing cells or tumors when the electric fields are applied to using an electronic device. More specifically, these electric fields fall into a special intermediate category, namely bio-effective fields that have no meaningful stimulatory and no thermal effects, and therefore overcome the disadvantages that were associated with the application of conventional electric fields to a body. It will also be appreciated that the present apparatus can further include a device for rotating the TC field relative to the living tissue. For example and according to one embodiment, the alternating electric potential applies to the tissue being treated is rotated relative to the tissue using conventional devices, such as a mechanical device that upon activation, rotates various components of the present system.

Moreover and according to yet another embodiment, the TC fields are applied to different pairs of the insulated electrodes 230 in a consecutive manner. In other words, the generator 210 and the control system thereof can be arranged so that signals are sent at periodic intervals to select pairs of insulated electrodes 230, thereby causing the generation of the TC fields of different directions by these insulated electrodes 230. Because the signals are sent at select times from the generator to the insulated electrodes 230, the TC fields of changing directions are generated consecutively by different insulated electrodes 230. This arrangement has a number of advantages and is provided in view of the fact that the TC fields have maximal effect when they are parallel to the axis of cell division. Since the orientation of cell division is in most cases random, only a fraction of the dividing cells are affected by any given field. Thus, using fields of two or more orientations increases the effectiveness since it increases the chances that more dividing cells are affected by a given TC field.

Figure 26:
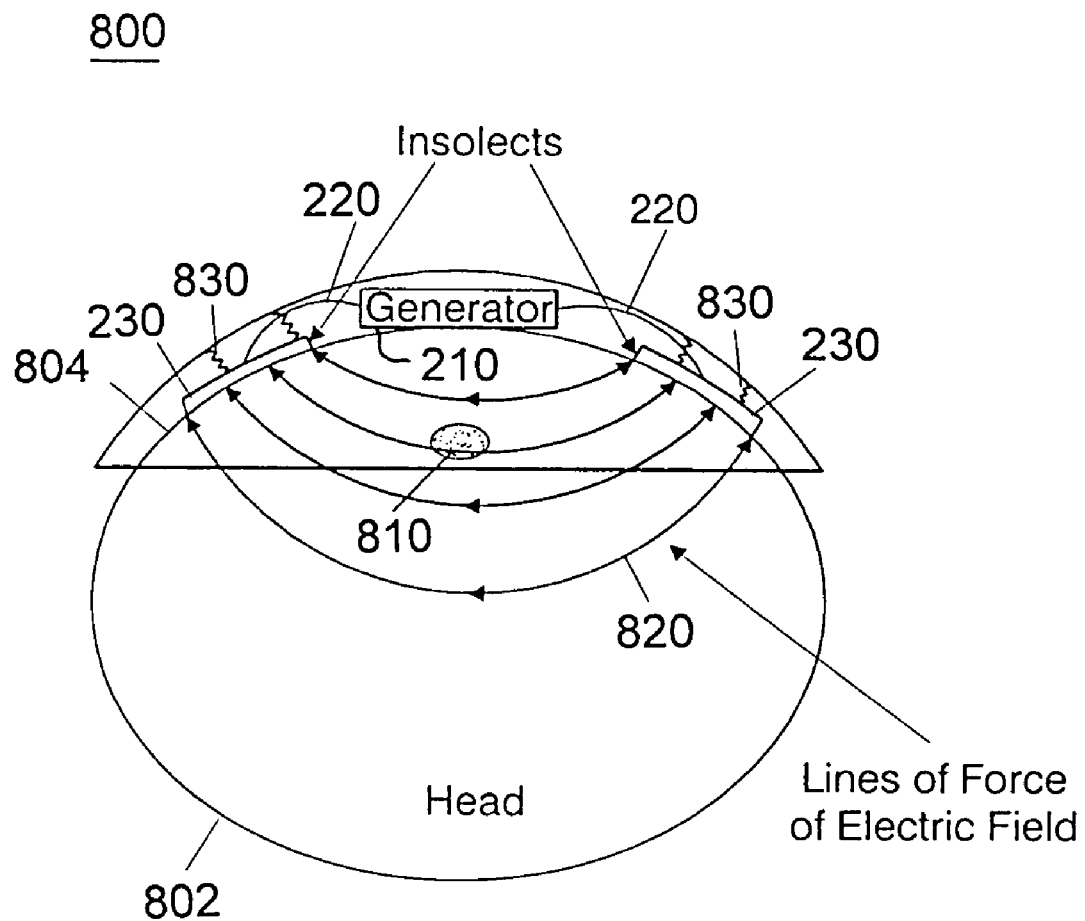

Turning now to FIG. 26 in which an article of clothing 800 according to one exemplary embodiment is illustrated. More specifically, the article of clothing 800 is in the form of a hat or cap or other type of clothing designed for placement on a head of a person. For purposes of illustration, a head 802 is shown with the hat 800 being placed thereon and against a skin surface 804 of the head 802. An intra-cranial tumor or the like 810 is shown as being formed within the head 802 underneath the skin surface 804 thereof. The hat 800 is therefore intended for placement on the head 802 of a person who has a tumor 810 or the like.

Unlike the various embodiments illustrated in the other Figures where the insulated electrodes 230 are arranged in a more or less planar arrangement since they are placed either on a skin surface or embedded within the body underneath it, the insulated electrodes 230 in this embodiment are specifically contoured and arranged for a specific application. The treatment of intra-cranial tumors or other lesions or the like typically requires a treatment that is of a relatively long duration, e.g., days to weeks, and therefore, it is desirable to provide as much comfort as possible to the patient. The hat 800 is specifically designed to provide comfort during the lengthy treatment process while not jeopardizing the effectiveness of the treatment.

According to one exemplary embodiment, the hat 800 includes a predetermined number of insulated electrodes 230 that are preferably positioned so as to produce the optimal TC fields at the location of the tumor 810. The lines of force of the TC field are generally indicated at 820. As can be seen in FIG. 26, the tumor 810 is positioned within these lines of force 820. As will be described in greater detail hereinafter, the insulated electrodes 230 are positioned within the hat 800 such that a portion or surface thereof is free to contact the skin surface 804 of the head 802. In other words, when the patient wears the hat 800, the insulated electrodes 230 are placed in contact with the skin surface 804 of the head 802 in positions that are selected so that the TC fields generated thereby are focused at the tumor 810 while leaving surrounding areas in low density. Typically, hair on the head 802 is shaved in selected areas to permit better contact between the insulated electrodes 230 and the skin surface 804; however, this is not critical.

The hat 800 preferably includes a mechanism 830 that applies or force to the insulated electrodes 230 so that they are pressed against the skin surface 802. For example, the mechanism 830 can be of a biasing type that applies a biasing force to the insulated electrodes 230 to cause the insulated electrodes 230 to be directed outwardly away from the hat 800. Thus, when the patient places the hat 800 on his/her head 802, the insulated electrodes 230 are pressed against the skin surface 804 by the mechanism 830. The mechanism 830 can slightly recoil to provide a comfortable fit between the insulated electrodes 230 and the head 802. In one exemplary embodiment, the mechanism 830 is a spring based device that is disposed within the hat 800 and has one section that is coupled to and applies a force against the insulated electrodes 230, as described below with reference to FIGS. 27 and 28.

As with the prior embodiments, the insulated electrodes 230 are coupled to the generator 210 by means of conductors 220. The generator 210 can be either disposed within the hat 800 itself so as to provide a compact, self-sufficient, independent system or the generator 210 can be disposed external to the hat 800 with the conductors 220 exiting the hat 800 through openings or the like and then running to the generator 210. When the generator 210 is disposed external to the hat 800, it will be appreciated that the generator 210 can be located in any number of different locations, some of which are in close proximity to the hat 800 itself, while others can be further away from the hat 800. For example, the generator 210 can be disposed within a carrying bag or the like (e.g., a bag that extends around the patient's waist) which is worn by the patient or it can be strapped to an extremity or around the torso of the patient. The generator 210 can also be disposed in a protective case that is secured to or carried by another article of clothing that is worn by the patient. For example, the protective case can be inserted into a pocket of a sweater, etc. FIG. 26 illustrates an embodiment where the generator 210 is incorporated directly into the hat 800.

Figure 27:
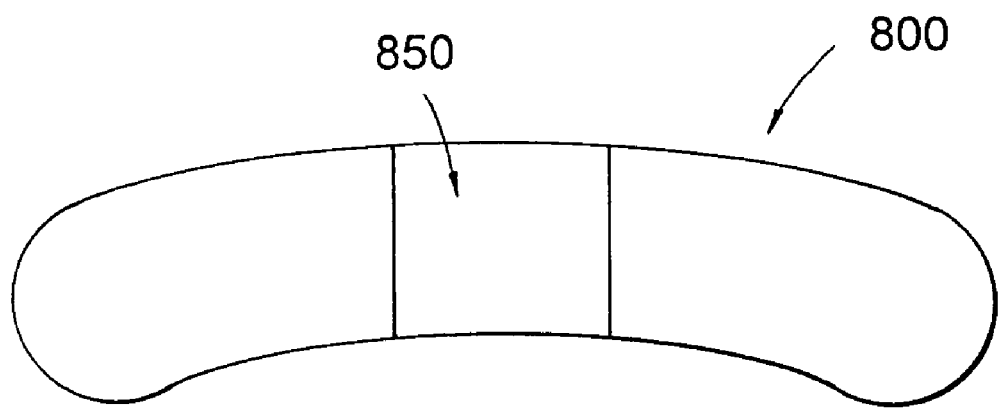
FIG. 27 is a partial section of a hat according to an exemplary embodiment having a recessed section for receiving one or more insulated electrodes.
Figure 28:
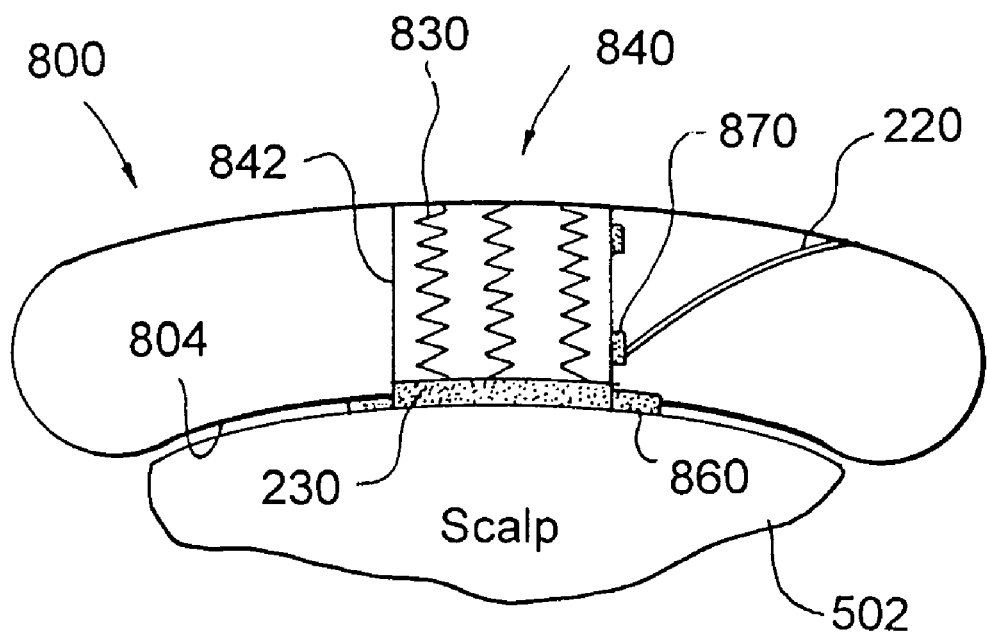
FIG. 28 is a cross-sectional view of the hat of FIG. 27 placed on a head and illustrating a biasing mechanism for applying a force to the insulated electrode to ensure the insulated electrode remains in contact against the head.

Turning now to FIGS. 27 and 28, in one exemplary embodiment, a number of insulated electrodes 230 along with the mechanism 830 are preferably formed as an independent unit, generally indicated at 840, that can be inserted into the hat 800 and electrically connected to the generator (not shown) via the conductors (not shown). By providing these members in the form of an independent unit, the patient can easily insert and/or remove the units 840 from the hat 800 when they may need cleaning, servicing and/or replacement.

In this embodiment, the hat 800 is constructed to include select areas 850 that are formed in the hat 800 to receive and hold the units 840. For example and as illustrated in FIG. 27, each area 850 is in the form of an opening (pore) that is formed within the hat 800. The unit 840 has a body 842 and includes the mechanism 830 and one or more insulated electrodes 230. The mechanism 830 is arranged within the unit 840 so that a portion thereof (e.g., one end thereof) is in contact with a face of each insulated electrode 230 such that the mechanism 830 applies a biasing force against the face of the insulated electrode 230. Once the unit 840 is received within the opening 850, it can be securely retained therein using any number of conventional techniques, including the use of an adhesive material or by using mechanical means. For example, the hat 800 can include pivotable clip members that pivot between an open position in which the opening 850 is free and a closed position in which the pivotable clip members engage portions (e.g., peripheral edges) of the insulated electrodes to retain and hold the insulated electrodes 230 in place. To remove the insulated electrodes 230, the pivotable clip members are moved to the open position. In the embodiment illustrated in FIG. 28, the insulated electrodes 230 are retained within the openings 850 by an adhesive element 860 which in one embodiment is a two sided self-adhesive rim member that extends around the periphery of the insulated electrode 230. In other words, a protective cover of one side of the adhesive rim 860 is removed and it is applied around the periphery of the exposed face of the insulated electrode 230, thereby securely attaching the adhesive rim 860 to the hat 800 and then the other side of the adhesive rim 860 is removed for application to the skin surface 804 in desired locations for positioning and securing the insulated electrode 230 to the head 802 with the tumor being positioned relative thereto for optimization of the TC fields. Since one side of the adhesive rim 860 is in contact with and secured to the skin surface 840, this is why it is desirable for the head 802 to be shaved so that the adhesive rim 860 can be placed flushly against the skin surface 840.

The adhesive rim 860 is designed to securely attach the unit 840 within the opening 850 in a manner that permits the unit 840 to be easily removed from the hat 800 when necessary and then replaced with another unit 840 or with the same unit 840. As previously mentioned, the unit 840 includes the biasing mechanism 830 for pressing the insulated electrode 230 against the skin surface 804 when the hat 800 is worn. The unit 840 can be constructed so that side opposite the insulated electrode 230 is a support surface formed of a rigid material, such as plastic, so that the biasing mechanism 830 (e.g., a spring) can be compressed therewith under the application of force and when the spring 830 is in a relaxed state, the spring 830 remains in contact with the support surface and the applies a biasing force at its other end against the insulated electrode 230. The biasing mechanism 830 (e.g., spring) preferably has a contour corresponding to the skin surface 804 so that the insulated electrode 230 has a force applied thereto to permit the insulated electrode 230 to have a contour complementary to the skin surface 804, thereby permitting the two to seat flushly against one another. While the mechanism 830 can be a spring, there are a number of other embodiments that can be used instead of a spring. For example, the mechanism 830 can be in the form of an elastic material, such as a foam rubber, a foam plastic, or a layer containing air bubbles, etc.

The unit 840 has an electric connector 870 that can be hooked up to a corresponding electric connector, such as a conductor 220, that is disposed within the hat 800. The conductor 220 connects at one end to the unit 840 and at the other end is connected to the generator 210. The generator 210 can be incorporated directly into the hat 800 or the generator 210 can be positioned separately (remotely) on the patient or on a bedside support, etc.

As previously discussed, a coupling agent, such as a conductive gel, is preferably used to ensure that an effective conductive environment is provided between the insulated electrode 230 and the skin surface 804. Suitable gel materials have been disclosed hereinbefore in the discussion of earlier embodiments. The coupling agent is disposed on the insulated electrode 230 and preferably, a uniform layer of the agent is provided along the surface of the electrode 230. One of the reasons that the units 840 need replacement at periodic times is that the coupling agent needs to be replaced and/or replenished. In other words, after a predetermined time period or after a number of uses, the patient removes the units 840 so that the coupling agent can be applied again to the electrode 230.

Figure 29:
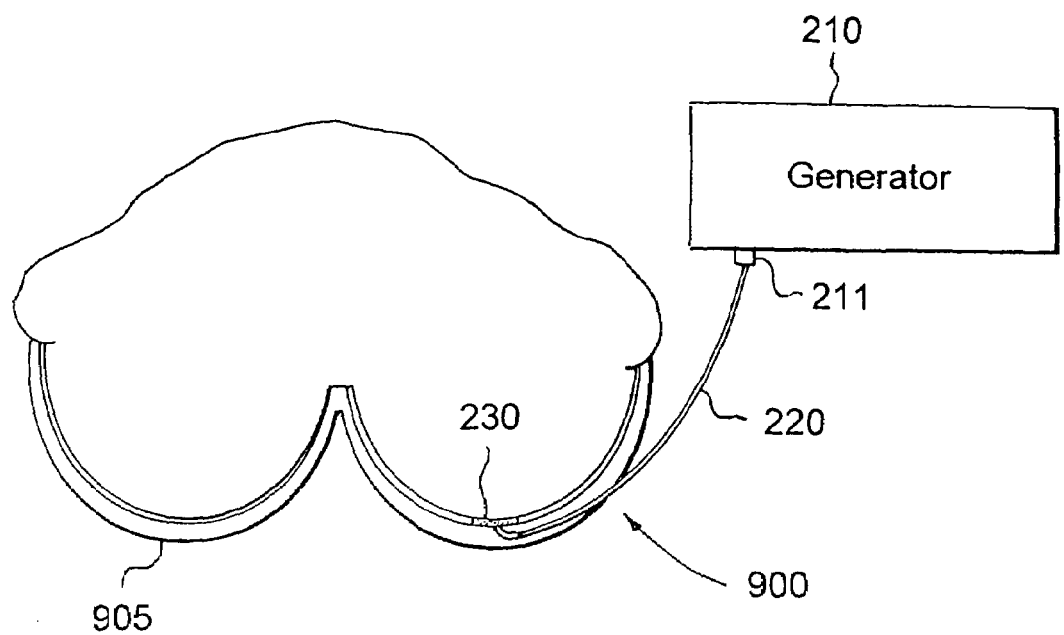
Figure 30:
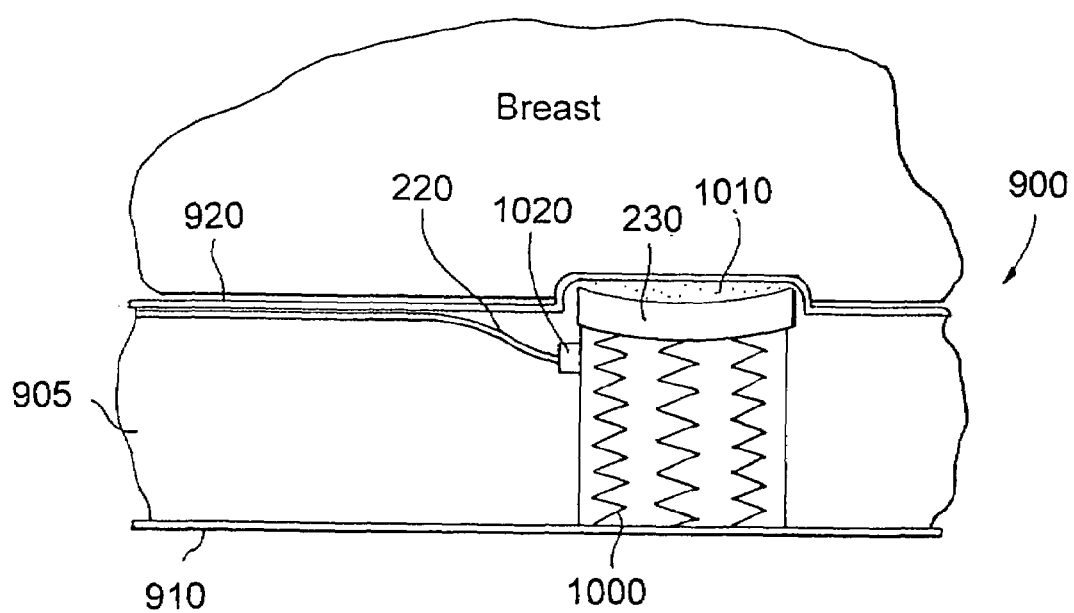
FIG. 30 is a cross-sectional view of a section of the article of clothing of FIG. 29 illustrating a biasing mechanism for biasing the insulated electrode in a direction to ensure the insulated electrode is placed proximate to a skin surface where treatment is desired.

FIGS. 29 and 30 illustrate another article of clothing which has the insulated electrodes 230 incorporated as part thereof. More specifically, a bra or the like 900 is illustrated and includes a body that is formed of a traditional bra material, generally indicated at 905, to provide shape, support and comfort to the wearer. The bra 900 also includes a fabric support layer 910 on one side thereof. The support layer 910 is preferably formed of a suitable fabric material that is constructed to provide necessary and desired support to the bra 900.

Similar to the other embodiments, the bra 900 includes one or more insulated electrodes 230 disposed within the bra material 905. The one or more insulated electrodes are disposed along an inner surface of the bra 900 opposite the support 910 and are intended to be placed proximate to a tumor or the like that is located within one breast or in the immediately surrounding area. As with the previous embodiment, the insulated electrodes 230 in this embodiment are specifically constructed and configured for application to a breast or the immediate area. Thus, the insulated electrodes 230 used in this application do not have a planar surface construction but rather have an arcuate shape that is complementary to the general curvature found in a typical breast.

A lining 920 is disposed across the insulated electrodes 230 so as to assist in retaining the insulated electrodes in their desired locations along the inner surface for placement against the breast itself. The lining 920 can be formed of any number of thin materials that are comfortable to wear against one's skin and in one exemplary embodiment, the lining 920 is formed of a fabric material.

The bra 900 also preferably includes a biasing mechanism 1000 as in some of the earlier embodiments. The biasing mechanism 1000 is disposed within the bra material 905 and extends from the support 910 to the insulated electrode 230 and applies a biasing force to the insulated electrode 230 so that the electrode 230 is pressed against the breast. This ensures that the insulated electrode 230 remains in contact with the skin surface as opposed to lifting away from the skin surface, thereby creating a gap that results in a less effective treatment since the gap diminishes the efficiency of the TC fields. The biasing mechanism 1000 can be in the form of a spring arrangement or it can be an elastic material that applies the desired biasing force to the insulated electrodes 230 so as to press the insulated electrodes 230 into the breast. In the relaxed position, the biasing mechanism 1000 applies a force against the insulated electrodes 230 and when the patient places the bra 900 on their body, the insulated electrodes 230 are placed against the breast which itself applies a force that counters the biasing force, thereby resulting in the insulated electrodes 230 being pressed against the patient's breast. In the exemplary embodiment that is illustrated, the biasing mechanism 1000 is in the form of springs that are disposed within the bra material 905.

A conductive gel 1010 can be provided on the insulated electrode 230 between the electrode and the lining 920. The conductive gel layer 1010 is formed of materials that have been previously described herein for performing the functions described above.

An electric connector 1020 is provided as part of the insulated electrode 230 and electrically connects to the conductor 220 at one end thereof, with the other end of the conductor 220 being electrically connected to the generator 210. In this embodiment, the conductor 220 runs within the bra material 905 to a location where an opening is formed in the bra 900. The conductor 220 extends through this opening and is routed to the generator 210, which in this embodiment is disposed in a location remote from the bra 900. It will also be appreciated that the generator 210 can be disposed within the bra 900 itself in another embodiment. For example, the bra 900 can have a compartment formed therein which is configured to receive and hold the generator 210 in place as the patient wears the bra 900. In this arrangement, the compartment can be covered with a releasable strap that can open and close to permit the generator 210 to be inserted therein or removed therefrom. The strap can be formed of the same material that is used to construct the bra 900 or it can be formed of some other type of material. The strap can be releasably attached to the surrounding bra body by fastening means, such as a hook and loop material, thereby permitting the patient to easily open the compartment by separating the hook and loop elements to gain access to the compartment for either inserting or removing the generator 210.

The generator 210 also has a connector 211 for electrical connection to the conductor 220 and this permits the generator 210 to be electrically connected to the insulated electrodes 230.

As with the other embodiments, the insulated electrodes 230 are arranged in the bra 900 to focus the electric field (TC fields) on the desired target (e.g., a tumor). It will be appreciated that the location of the insulated electrodes 230 within the bra 900 will vary depending upon the location of the tumor. In other words, after the tumor has been located, the physician will then devise an arrangement of insulated electrodes 230 and the bra 900 is constructed in view of this arrangement so as to optimize the effects of the TC fields on the target area (tumor). The number and position of the insulated electrodes 230 will therefore depend upon the precise location of the tumor or other target area that is being treated. Because the location of the insulated electrodes 230 on the bra 900 can vary depending upon the precise application, the exact size and shape of the insulated electrodes 230 can likewise vary. For example, if the insulated electrodes 230 are placed on the bottom section of the bra 900 as opposed to a more central location, the insulated electrodes 230 will have different shapes since the shape of the breast (as well as the bra) differs in these areas.

Figure 31:
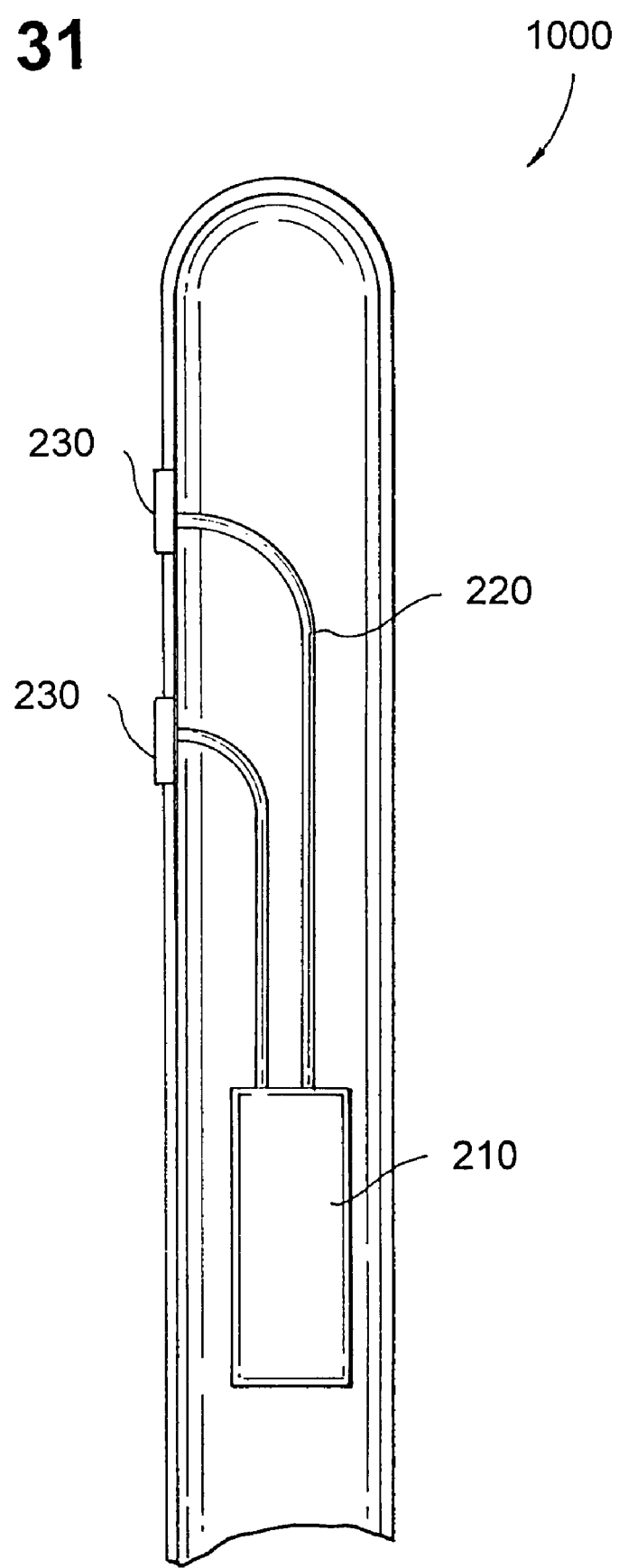

FIG. 31 illustrates yet another embodiment in which the insulated electrodes 230 are in the form of internal electrodes that are incorporated into in the form of a probe or catheter 1100 that is configured to enter the body through a natural pathway, such as the urethra, vagina, etc. In this embodiment, the insulated electrodes 230 are disposed on an outer surface of the probe 1100 and along a length thereof. The conductors 220 are electrically connected to the electrodes 230 and run within the body of the probe 1100 to the generator 210 which can be disposed within the probe body or the generator 210 can be disposed independent of the probe 1100 in a remote location, such as on the patient or at some other location close to the patient.

Alternatively, the probe 1100 can be configured to penetrate the skin surface or other tissue to reach an internal target that lies within the body. For example, the probe 1100 can penetrate the skin surface and then be positioned adjacent to or proximate to a tumor that is located within the body.

In these embodiments, the probe 1100 is inserted through the natural pathway and then is positioned in a desired location so that the insulated electrodes 230 are disposed near the target area (i.e., the tumor). The generator 210 is then activated to cause the insulated electrodes 230 to generate the TC fields which are applied to the tumor for a predetermined length of time. It will be appreciated that the illustrated probe 1100 is merely exemplary in nature and that the probe 1100 can have other shapes and configurations so long as they can perform the intended function. Preferably, the conductors (e.g., wires) leading from the insulated electrodes 230 to the generator 210 are twisted or shielded so as not to generate a field along the shaft.

It will further be appreciated that the probes can contain only one insulated electrode while the other can be positioned on the body surface. This external electrode should be larger or consist of numerous electrodes so as to result in low lines of force-current density so as not to affect the untreated areas. In fact, the placing of electrodes should be designed to minimize the field at potentially sensitive areas.

Figure 32:
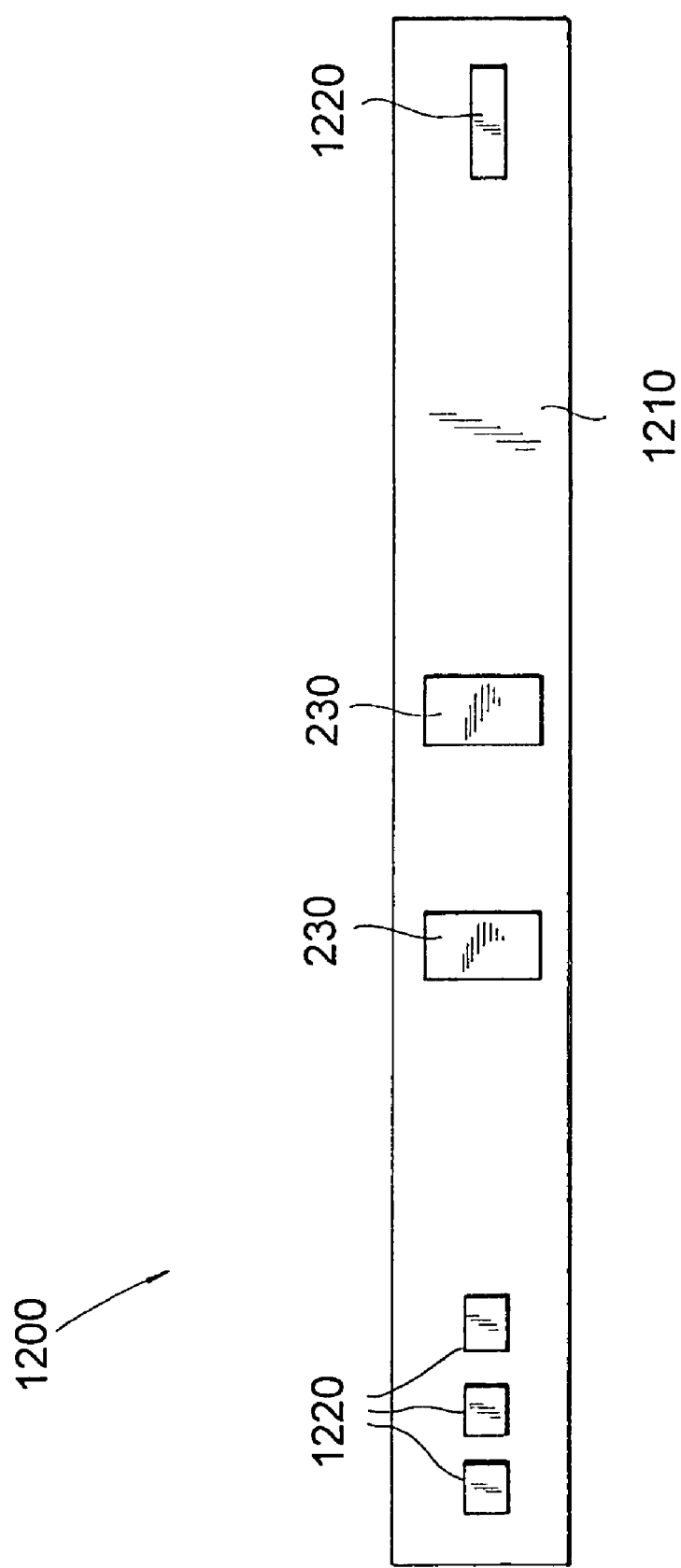
FIG. 32 is an elevation view of an unwrapped collar according to one exemplary embodiment for placement around a neck for treating a tumor or the like in the area where the collar is wrapped around the neck.

FIG. 32 illustrates yet another embodiment in which a high standing collar member 1200 (or necklace type structure) can be used to treat thyroid, parathyroid, laryngeal lesions, etc. FIG. 32 illustrates the collar member 1200 in an unwrapped, substantially flat condition. In this embodiment, the insulated electrodes 230 are incorporated into a body 1210 of the collar member 1200 and are configured for placement against a neck area of the wearer. The insulated electrodes 230 are coupled to the generator 210 according to any of the manner described hereinbefore and it will be appreciated that the generator 210 can be disposed within the body 1210 or it can be disposed in a location external to the body 1210. The collar body 1210 can be formed of any number of materials that are traditionally used to form collars 1200 that are disposed around a person's neck. As such, the collar 1200 preferably includes a means 1220 for adjusting the collar 1200 relative to the neck. For example, complementary fasteners (hook and loop fasteners, buttons, etc.) can be disposed on ends of the collar 1200 to permit adjustment of the collar diameter. It will be appreciated that one can extend this exemplary structure to accommodate any tubular part of the body, e.g., a limb, etc.

Figure 33:
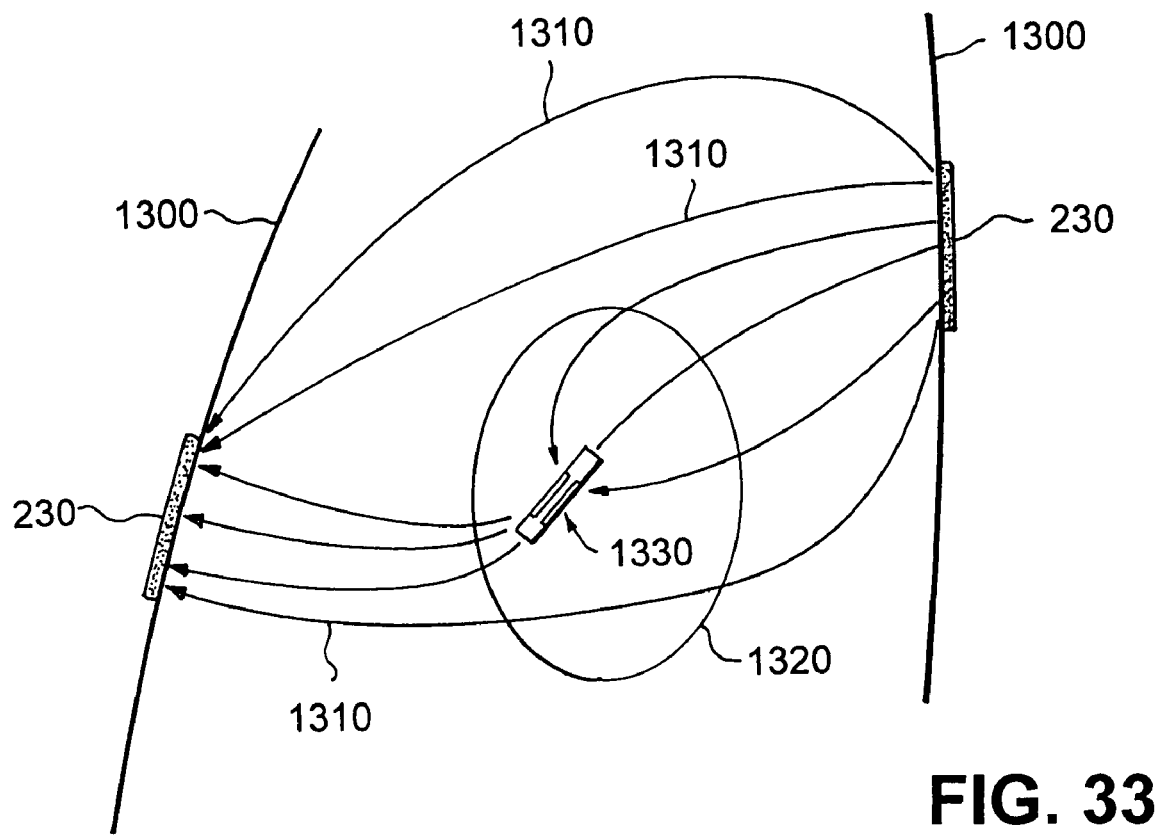
FIG. 33 is a side elevation view of the present apparatus being used to prevent restenosis of arteries after angioplasty.
Figure 34:
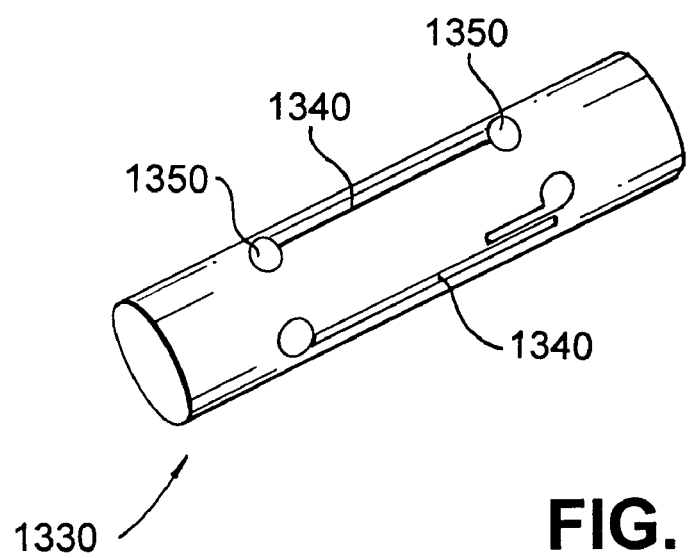
FIG. 34 is an enlarged view of a stent used in the arrangement of FIG. 33.

FIGS. 33 and 34 illustrate yet another embodiment of the present device. In FIG. 33, a pair of electrodes 230 are arranged about a torso 1300. The electrodes 230 are operated in the same manner as was previously described and in this embodiment, the electrodes 230 are arranged so that the electric field passes through the heart and its surrounding area.

The present inventor has thus appreciated that the above described TC fields that stop cell proliferation can be used to prevent restenosis of arteries after angioplasty, with or without introduction of stents. This also applies for other body tubing, such as urethra. The coronary restenosis which follows 20–30% of stenting, etc., is a major problem. The restenosis is due to the cellular reaction of the arterial wall and the resulting cell proliferation. This proliferation grows into the artery from its ends and on top of it, there is sedimentation, etc., that occludes the artery. The conditions for the effect of the TC fields are good as the stent is usually a bare metal conductor (but not necessarily) that will result in field intensification exactly where it is needed. The TC fields should be applied for 3–8 weeks to prevent the stenosis.

As shown in FIGS. 33 and 34, the electrodes 230 are arranged about the torso 1300 so that the TC fields, indicated by field lines 1310, passes through the heart region 1320. A coronary artery 1330 is illustrated within the heart region 1320 and within the TC fields. One or more stents 1340 are disposed within the coronary artery 1330 as part of the surgical procedure. One of the results of the angioplasty and mainly due to the presence of the stents 1340 is a proliferation of a mass of cells 1350 that is located along the artery wall. Since the stent 1340 acts as a conductor, the area around the stent 1340 is an area of high density electric field due to the presence of the stent 1340. The stent 1340 does not necessarily have to be a bare metal conductor and the present method of treatment can be used without stents 1340 so long as the mass of proliferating cells 1350 is disposed within the area of the high density electric field.

Thus, the construction of the present devices are particularly well suited for applications where the devices are incorporated into articles of clothing to permit the patient to easily wear a traditional article of clothing while at the same time the patient undergoes treatment. In other words, an extra level of comfort can be provided to the patient and the effectiveness of the treatment can be increased by incorporating some or all of the device components into the article of clothing. The precise article of clothing that the components are incorporated into will obviously vary depending upon the target area of the living tissue where tumor, lesion or the like exists. For example, if the target area is in the testicle area of a male patient, then an article of clothing in the form of a sock-like structure or wrap can be provided and is configured to be worn around the testicle area of the patient in such a manner that the insulated electrodes thereof are positioned relative to the tumor such that the TC fields are directed at the target tissue. The precise nature or form of the article of clothing can vary greatly since the device components can be incorporated into most types of articles of clothing and therefore, can be used to treat any number of different areas of the patient's body where a condition may be present.

The present invention is thus for an apparatus and method for optimizing the selective destruction of dividing cells by calculating the spatial and temporal distribution of the electric fields for optimal treatment of a specific patient with a specific tumor, taking into account its location and characteristics of all components of the system. An optimal field map is generated by calculating and computing an electric field in terms of its strength and other characteristics for a given arrangement of electrodes and based on other inputted information, such as tumor type. This calculation can be done by a controller or other device, such as an integrated personal computer, and additional calculations are conducted for different arrangement of electrodes relative to the target area (tumor) and/or different voltages for the electrodes. Standard optimization methods are used to determine the optimal minimal field map. It is therefore desirable that the optimum field map not only includes a maximum electric field at the target area (tumor) but also that there be a maximal field strength difference between the electric field at the target tissue and the surrounding tissue that is to be protected. It will therefore be appreciated that the optimal field may not necessarily be one that has the highest electric field strength focused at the targeted area but it may be one where the electric field strength is less but the difference in field strength between the target area and the surrounding areas is at a maximum. In other words, the present method optimizes the correlation between the calculated electric field and the desired electric field (the previously calculated optimal field map). For optimization, standard techniques can be used, such as the Nelder-Mead simplex method.

As used herein, the term "tumor" refers to a malignant tissue comprising transformed cells that grow uncontrollably. Tumors include leukemias, lymphomas, myelomas, plasmacytomas, and the like; and solid tumors. Examples of solid tumors that can be treated according to the invention include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Because each of these tumors undergoes rapid growth, any one can be treated in accordance with the invention. The invention is particularly advantageous for treating brain tumors, which are difficult to treat with surgery and radiation, and often inaccessible to chemotherapy or gene therapies. In addition, the present invention is suitable for use in treating skin and breast tumors because of the ease of localized treatment provided by the present invention.

In addition, the present invention can control uncontrolled growth associated with non-malignant or pre-malignant conditions, and other disorders involving inappropriate cell or tissue growth by application of an electric field in accordance with the invention to the tissue undergoing inappropriate growth. For example, it is contemplated that the invention is useful for the treatment of arteriovenous (AV) malformations, particularly in intracranial sites. The invention may also be used to treat psoriasis, a dermatologic condition that is characterized by inflammation and vascular proliferation; and benign prostatic hypertrophy, a condition associated with inflammation and possibly vascular proliferation. Treatment of other hyperproliferative disorders is also contemplated.

Furthermore, undesirable fibroblast and endothelial cell proliferation associated with wound healing, leading to scar and keloid formation after surgery or injury, and restenosis after angioplasty or placement of coronary stents can be inhibited by application of an electric field in accordance with the present invention. The non-invasive nature of this invention makes it particularly desirable for these types of conditions, particularly to prevent development of internal scars and adhesions, or to inhibit restenosis of coronary, carotid, and other important arteries.

Thus, the present invention provides an effective, simple method of selectively destroying dividing cells, e.g., tumor cells and parasitic organisms, while non-dividing cells or organisms are left affected by application of the method on living tissue containing both types of cells or organisms. Thus, unlike many of the conventional methods, the present invention does not damage the normal cells or organisms. In addition, the present invention does not discriminate based upon cell type (e.g., cells having differing sizes) and therefore may be used to treat any number of types of sizes having a wide spectrum of characteristics, including varying dimensions.

It will be appreciated by persons skilled in the art that the present invention is not limited to the embodiments described thus far with reference to the accompanying drawing. Rather the present invention is limited only by the following claims.

What is claimed is:

1. A method for optimizing the selective destruction of dividing cells in a malcontrolled cell growth using a device that subjects the cell growth to an alternating electric field, wherein passage of the electric field through the dividing cells in late anaphase or telophase transforms the electric field into a non-homogeneous electric field that produces an increased density electric field in a region of the dividing cells to induce a structural change in the dividing cell resulting in destruction thereof, the optimization method comprising the steps of:

computing an optimal field map of the positions of electrodes relative to the malcontrolled cell growth in a target area;

arranging the electrodes according to a select pattern relative to the malcontrolled cell growth and computing a vector sum of electric fields to generate an electric field map;

comparing the electric field map to the optimal field map;

changing one of a delivered voltage to the electrodes and a location of the electrodes and computing a vector sum of electric fields to generate an electric field map for the electrodes; and optimizing a correlation between the generated electric field map and the optimal field map, wherein the step of optimizing a correlation takes into account an electrode voltage, a wave shape and a position of each electrode, and wherein the electric field is computed in accordance with the expression:

$$E = \frac{V}{r \ln\left(\frac{R_2}{R_1}\right)} \frac{\varepsilon_{coat}}{\varepsilon_{tissue}}$$

where $R_1$ is the radius of a conductive part of the electrode; $R_2$ is the electrode radius including a coating disposed on the electrode; and $\varepsilon_{coat}$ and $\varepsilon_{tissue}$ are the dielectric constants of the electrode coating and tissue, respectively and r is the distance between the electrodes to the point where one wants to calculate the electric field.

2. The method of claim 1, wherein the step of computing an optimal field map includes the steps of:
 (a) inputting characteristics of tissue cells in the target area;
 (b) inputting characteristic of the malcontrolled tissue cells in the target area;
 (c) inputting anatomical characteristic of the target area;
 (d) computing a threshold field intensity in the malcontrolled cell growth;
 (e) computing relative sensitivities of surrounding healthy tissue to the electric field;
 (f) computing a maximal allowed field intensity at predetermined location; and
 (g) computing the optimal field map on the basis of the information generated in step (a) to (f).

3. The method of claim 1, further comprising the step of: providing a device that includes:
 a first insulated electrode having a first conductor;
 a second insulated electrode having a second conductor; and
 an electric field source connected to the first and second insulated electrodes for applying the alternating electric field across the first and second conductors to creates a condition in the dividing cells that encourages the destruction thereof.

4. The method of claim 3, wherein, in the providing step, the first electrode includes a first dielectric member that is in contact with the first conductor, the first dielectric member for placement agaits the living tissue to form a capacitor and wherein the second electrode includes a second dielectric member that is contact with the second conductor, the second dielectric member for placement against the living tissue to form a capacitor.

5. The method of claim 1, wherein the alternating electric field has a frequency of between about 50 KHz to about 500 KHz.

6. The method of claim 1, wherein the alternating electric field has a frequency of between about 100 KHz to about 300 KHz.

7. The method of claim 3, wherein, in the providing step, the electric field source generates an alternating voltage waveform at frequencies between about 50 KHz to about 500 KHz.

8. The method of claim 7, including the step of:
 activating the first and second electrodes by the alternating voltage waveform.

9. The method of claim 1, wherein, in the providing step, the coating of the electrode comprises a potassium tantalate coating.

10. The method of claim 1, wherein the step of optimizing a correlation comprises the step of:
 applying a robust numeric optimization method to optimize the correlation between the generated electric field map and the optimal field map.

11. The method of claim 1, wherein the select pattern is one of a symmetric pattern and a non-symmetric pattern.

12. The method of claim 1, wherein the step of computing a vector sum comprises the steps of:
 feeding coordinates of all available electrodes; and
 computing the vector sum of the fields generated by each electrode at each point in time.

13. The method of claim 1, wherein the optimization step includes balancing the strength of the electric field at the malcontrolled cell growth and maximizing a difference between electric field strength at the malcontrolled cell growth and the electric field strength at surrounding healthy tissue.

14. The method of claim 1, wherein the tissue is muscle tissue and $\varepsilon_{tissue}$ equals $\varepsilon_{muscle}$.

15. A method to prevent restenosis of arteries after angioplasty, the method comprising the steps of:
 providing an apparatus having:
  a first insulated electrode;
  a second insulated electrode; and
  an electric field source for applying an alternating electric field across the first and second conductors;
 positioning the first and second insulated electrodes in relation to at least one mass of proliferating cells within at least one artery; and
 subjecting the one or more masses of proliferating cells to an alternating electric field, wherein passage of the electric field through the proliferating cells in late anaphase or telophase transforms the electric field into a non-homogeneous electric field that produces an increased density electric field in a region of the cells and induces a structural change in the cells resulting in destruction thereof, wherein subjecting the living tissue to the alternating electric field comprises applying an alternating electric potential having a frequency of between about 50 KHz to about 500 KHz.

16. The method of claim 15, wherein the step of positioning the first and second insulated electrodes comprises:
 placing the first and second electrodes against a chest wall and positioning the electrodes so that the heart and the at least one artery fall within a high density region of the electric field.

17. The method of claim 15, further including the step of:
 placing a stent within the at least one artery, the mass of proliferating cells growing at or near the stent.

18. The method of claim 17, wherein the stent comprises a conductive stent.

19. The method of claim 15, wherein, in the subjecting step, the alternating electric potential has a frequency of between about 100 KHz to about 300 KHz.

* * * * *

UNITED STATES PATENT AND TRADEMARK OFFICE
CERTIFICATE OF CORRECTION

PATENT NO.       : 7,146,210 B2                                    Page 1 of 1
APPLICATION NO.  : 10/402327
DATED            : December 5, 2006
INVENTOR(S)      : Yoram Palti It is certified that error appears in the above-identified patent and that said Letters Patent is hereby corrected as shown below:

Column 29
Line 28, change "characteristic" to --characteristics--.
Line 30, change "characteristic" to --characteristics--.
Line 34, change "field" to --fields--.
Line 36, change "location" to --locations--.
Line 38, change "step" to --steps--.
Line 47, change "creates" to --create--.
Line 52, change "againts" to --against--.
Line 54, change "is contact" to --is in contact--.

Signed and Sealed this

Thirteenth Day of March, 2007

JON W. DUDAS
*Director of the United States Patent and Trademark Office*